US011662283B2

(12) United States Patent
McCarty, II et al.

(10) Patent No.: US 11,662,283 B2
(45) Date of Patent: May 30, 2023

(54) SYSTEM FOR TENSILE TESTING FILMS

(71) Applicant: Dow Global Technologies LLC, Midland, MI (US)

(72) Inventors: Donald L. McCarty, II, Midland, MI (US); William E. Gee, Collegeville, PA (US); Paul OConnell, Lake Jackson, TX (US); Jonathan J. Zieman, Midland, MI (US); John Lund, Midland, MI (US); Hitendra Singh, Lake Jackson, TX (US); Scott J. Collick, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 449 days.

(21) Appl. No.: 16/630,754

(22) PCT Filed: Jun. 8, 2018

(86) PCT No.: PCT/US2018/036700
§ 371 (c)(1),
(2) Date: Jan. 13, 2020

(87) PCT Pub. No.: WO2019/027570
PCT Pub. Date: Feb. 7, 2019

(65) Prior Publication Data
US 2020/0166443 A1 May 28, 2020

Related U.S. Application Data

(60) Provisional application No. 62/539,340, filed on Jul. 31, 2017.

(51) Int. Cl.
*G01N 3/08* (2006.01)
*B25J 18/00* (2006.01)
(Continued)

(52) U.S. Cl.
CPC ............. *G01N 3/08* (2013.01); *B25J 18/00* (2013.01); *G01B 5/06* (2013.01); *G01B 11/02* (2013.01);
(Continued)

(58) Field of Classification Search
CPC .......... G01N 3/08; G01N 3/066; G01N 21/47; G01N 2203/0017; G01N 2203/006;
(Continued)

(56) References Cited

U.S. PATENT DOCUMENTS 2,340,401 A   2/1944  Martin
4,606,230 A   8/1986  Scott et al.
(Continued)

FOREIGN PATENT DOCUMENTS

JP      755669 A     1/1974
JP    52136622 S    10/1977
(Continued)

OTHER PUBLICATIONS

Shcherbina et al., "A Machine for Testing Thin Films with Automatic Recording of the Tensile Stress Diagram", Measurement Techniques, 1981, 1041-1042.
(Continued)

*Primary Examiner* — Jonathan M Dunlap
(74) *Attorney, Agent, or Firm* — Dinsmore & Shohl LLP

(57) ABSTRACT

A method and system for analyzing a physical characteristic of a film sample are described herein. The system may include a material holder system configured to hold the film sample. The system may include a tensile testing system configured to stretch the film sample and determine a physical characteristic of the film sample. The system may include a movable system coupled to the material holder system and configured to move the held film sample to be analyzed or tested between stations. The movable system is
(Continued)

configured to move the held film sample in the material holder system to the tensile testing system.

16 Claims, 17 Drawing Sheets

(51) Int. Cl.
    *G01B 5/06*     (2006.01)
    *G01B 11/02*     (2006.01)
    *G01N 3/06*     (2006.01)
    *G01N 21/47*     (2006.01)
    *G01N 21/88*     (2006.01)

(52) U.S. Cl.
    CPC ............. *G01N 3/066* (2013.01); *G01N 21/47* (2013.01); *G01N 21/88* (2013.01); *G01N 2203/006* (2013.01); *G01N 2203/0017* (2013.01); *G01N 2203/0206* (2013.01); *G01N 2203/0282* (2013.01); *G01N 2203/0617* (2013.01)

(58) Field of Classification Search
    CPC ... G01N 2203/0206; G01N 2203/0282; G01N 2203/0617; G01N 2203/0278; G01N 33/442; B25J 18/00; G01B 5/06; G01B 11/02
    See application file for complete search history.

(56) References Cited

U.S. PATENT DOCUMENTS

| | | | |
|---|---|---|---|
| 5,437,192 | A | 8/1995 | Kawamoto et al. |
| 6,139,889 | A | 10/2000 | Guinee et al. |
| 2010/0300195 | A1 | 12/2010 | Coulter et al. |
| 2013/0152706 | A1 | 6/2013 | Nam et al. |
| 2014/0079525 | A1* | 3/2014 | Krimpmann ......... B25J 15/0616 414/797 |
| 2021/0078193 | A1 | 3/2021 | McCarty, II et al. |

FOREIGN PATENT DOCUMENTS

| | | |
|---|---|---|
| JP | H04125445 A | 4/1992 |
| JP | 5126705 A | 5/1993 |
| JP | 06313751 | 7/1996 |
| JP | 10253474 A | 9/1998 |
| JP | 2000111463 A | 4/2000 |
| JP | 2000352551 A | 12/2000 |
| JP | 3340197 B2 | 11/2002 |
| JP | 2002365187 A | 12/2002 |
| JP | 3196252 U | 2/2015 |
| KR | 20040054970 A | 6/2004 |
| KR | 200170030299 A | 3/2017 |

OTHER PUBLICATIONS

International Search Report and Written Opinion pertaining to PCT/US2018/036700, dated Aug. 10, 2018.
Shcherbina, M.E., "Installation for Thin Film Testing with Automatic Recording", Translated from Izmeritel'naya Tekhnika, 1989, 29-30.
Japanese Office Action, dated Apr. 5, 2022 pertaining to Japanese Patent Application No. 2020-504006.
Communication Pursuant to Article 94(3) EPC pertaining to EP 19735101.0, dated Feb. 2, 2022.
Japanese Decision of Rejection dated Aug. 30, 2022, pertaining to Japanese Patent Application No. 2020-504006 3 pages.
Communication Pursuant to Article 94(3) dated Feb. 16, 2022, pertaining to EP 18731549.4.
International Search Report and Written Opinion pertaining to PCT/US2018/030210, dated Aug. 10, 2018.
Communication pursuant to Rules 161(1) and 162 EPC, dated Mar. 3, 2020, pertaining to EP18731549.4.
Japanese Office Action dated Apr. 5, 2022, pertaining to Japanese Patent Application No. 2020-503776.
Korean non-final Office Action, dated May 24, 2022, pertaining to Korean Patent Application No. 10-2020-7005147.
International Preliminary Report on Patentability PCT/US2018/030210 dated Feb. 4, 2020.
International Search Report and Written Opinion pertaining to PCT/US2018/030261, dated Aug. 10, 2018.
Examination Report dated Feb. 10, 2022, pertaining to EP Patent Application No. 18731551.0, 6 pages.
Notice of Allowance dated May 13, 2022 pertaining to U.S. Appl. No. 16/630,709 (13 pages total).

\* cited by examiner

SYSTEM FOR TENSILE TESTING FILMS

FIELD

The present invention relates to a system for tensile testing of films of material.

Introduction

Characterizing physical properties of materials is useful in analyzing and improving chemical formulations employed in the production of the materials as well as in analyzing and improving processes of manufacturing the materials. Characterizing the physical properties may also help consumers determine the best product for their particular use case, as well as help researchers develop novel solutions for specific applications.

One of the useful physical properties of a material is determining tensile strength of the material. The tensile test can be used, for example, for determining tensile properties of thin films as thin films are often used in packaging applications, such plastic wrap and packing tape. The suitability of a material for an intended purpose may depend on the ability of the material to withstand or give way during tensile stretching. In such instances, the chemical and physical characteristics of the material may affect the tensile resistance of the material. The tensile test usually involves stretching a material sample at a constant speed and measuring and recording the force that it exerts. A force curve is recorded and various material properties may be determined, such as Young's modulus, Poisson's ratio, yield strength, tensile strength, strain-hardening, etc., about the material sample.

The American Society for Testing and Materials (ASTM) has a set of standards that are widely used throughout the world for characterizing materials. Tensile testing is a popular test that is performed frequently across the plastics industry. Currently, tensile testing systems are available, such as from Zwick, Instron, and MTS. However, these instruments are not capable of providing unattended operation from sample preparation through analysis for multiple samples. Additionally, these instruments may require manual input of sample width and thickness. Additionally, the prior art systems are not capable of effectively testing non-rigid materials.

Therefore, a need remains for an automated system for tensile testing films that overcomes these and other drawbacks of the prior art.

SUMMARY

It was determined that by using a system for tensile testing films according to the present disclosure, the process for testing multiple film samples can be automated from sample preparation through testing, and throughput can be improved.

According to an embodiment of the disclosure, a system for analyzing a physical characteristic of a film sample may include a material holder system configured to hold the film sample, a tensile testing system configured to stretch the film sample and determine a physical characteristic of the film sample, and a movable system coupled to the material holder system and configured to move the held film sample to be analyzed or tested between stations. The movable system is configured to move the held film sample in the material holder system to the tensile testing system.

According to an embodiment of the disclosure, a method for analyzing a physical characteristic of a film sample may include holding the film sample with a material holder system connected to a movable system, testing a physical characteristic of the film sample with a tensile testing apparatus, and moving the material holder system holding the film sample to the tensile testing system with the movable system.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

According to embodiments of the present disclosure, the process of tensile testing films of material, such as thin films, may be automated. Automated tensile testing systems can provide for high throughput (HTP) testing of films in various industries. A higher rate of testing means large amounts of data can be gathered relatively quickly and analyzed for trends, allowing more detailed studies to be conducted on areas of interest. Embodiments of the present disclosure provide continuous (or near continuous) operation, allowing systems to run effectively non-stop and increasing the amount of testing performed. The system also allows an increase of the speed of a single test as compared to manual test systems. According to embodiments of the present disclosure, this is accomplished using robotics to take the place of a human researcher or operator. According to embodiments of the present disclosure, a second feature that may be used for increasing throughput of a system without sacrificing accuracy is to perform multiple tests in parallel. A third feature is that the system is repeatable and uniform as compared to human-based testing systems. By employing one or more of the foregoing features, embodiments of the present disclosure can increase the number of film samples tested. For example, according to embodiments of the present disclosure, a 6"×6" (152 mm×152 mm) film sample may be tested every 2 minutes. The tensile testing and subsequent tensile properties analysis of the films provides tensile strength and ultimate tensile strength data with correlation to ASTM D882.

According to embodiments of the present disclosure, tensile testing systems for thin films can be integrated with a blown film fabrication line, or integrated into an existing blown film lab. Tensile testing systems according to embodiments of the present disclosure allow tests to be conducted automatically and relatively quickly, allowing film labs to clear out their backlog of tests. Although the following disclosure discusses tensile testing of thin films, it will be understood that the system of the present invention can be used for determining properties of many types of materials, including polymers, plastics, rubber, blow-molded films, polyethylene based films, and non-polymeric materials.

Figure 1:
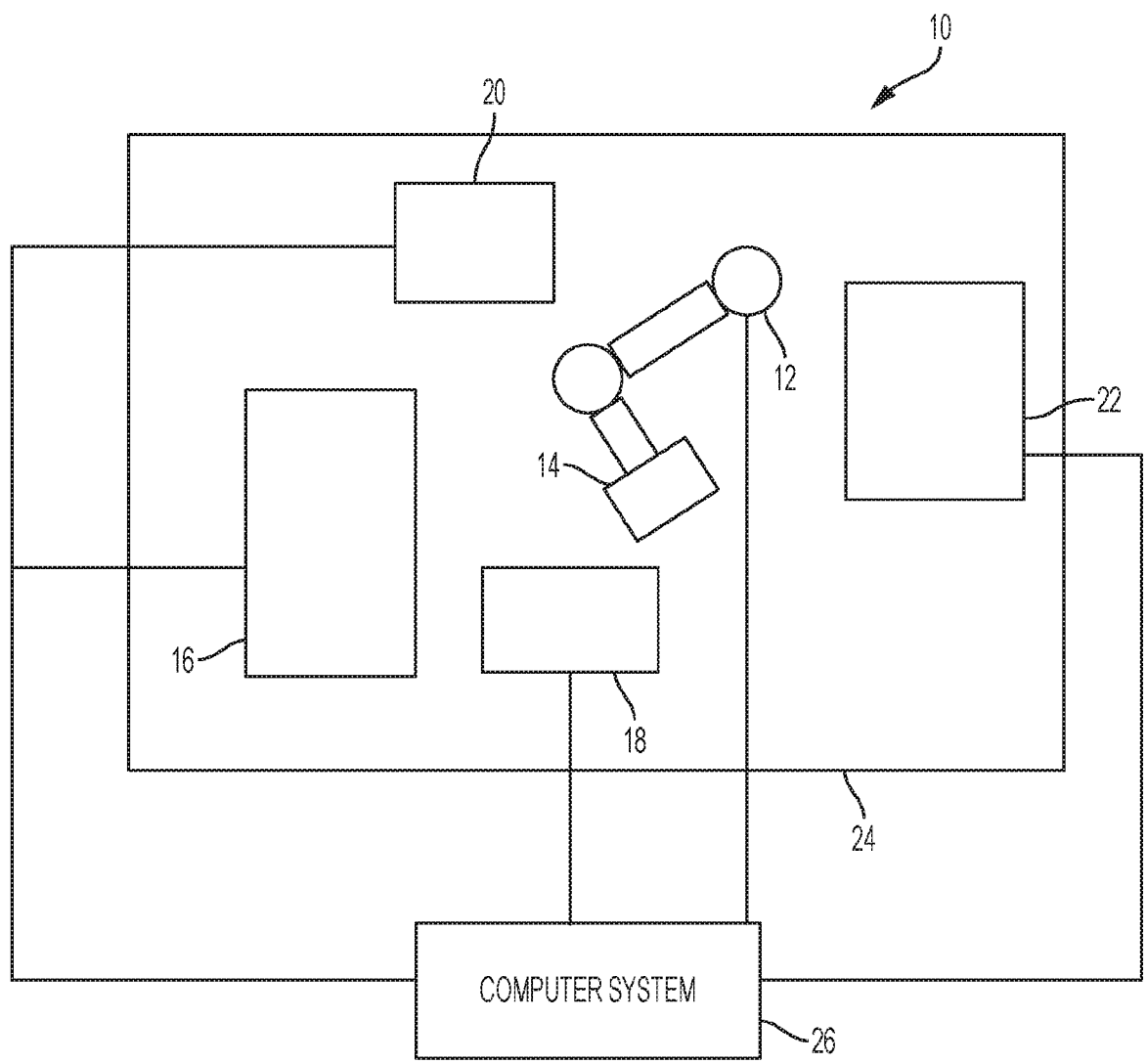
FIG. 1 shows a schematic diagram of a system according to an embodiment of the present disclosure.

FIG. 1 shows a schematic diagram of a tensile testing system 10 according to an embodiment of the present disclosure. In an embodiment of the present disclosure, the tensile testing system 10 includes a movable system, such as a robotic system 12, a material holder system 14, a cutting device 16, a material image analyzer system 18, a material thickness measurement system 20, and a tensile testing apparatus 22. The robotic system 12, the material holder system 14, the cutting device 16, the material image analyzer system 18, the material thickness measurement system 20, and/or the tensile testing apparatus 22 can be provided on work surface 24 or a common framework. The robotic system 12, the material holder system 14, the cutting device 16, the material image analyzer system 18, the material thickness measurement system 20, and/or the tensile testing apparatus 22 can be controlled using computer system 26.

Figure 2:
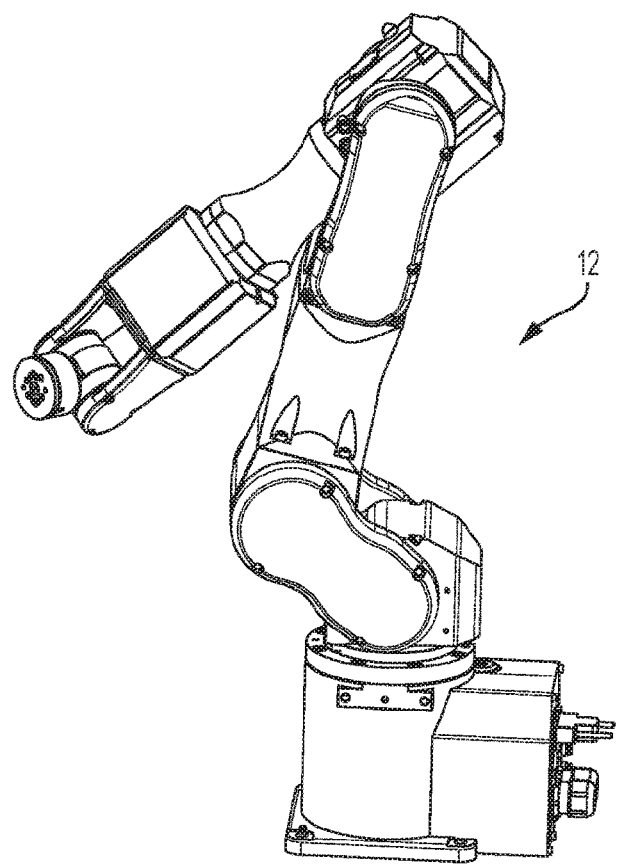
FIG. 2 shows a three-dimensional perspective view of a robotic system, according to an embodiment of the present disclosure.

FIG. 2 shows a three-dimensional perspective view of the robotic system 12, according to an embodiment of the present disclosure. In an embodiment, the robotic system 12 is a six-axis robotic arm system such as Epson C4 robot made by Epson Corporation. The robotic system 12 is configured to move a film sample to be tested between stations provided on the work surface 24 or common framework. Although a six-axis robotic arm system 12 is described, the robotic system 12 may be any system capable of being connected to the material holder system 14 and capable of moving a film in multiple planes around the work surface 24. The robotic system 12 may be any articulating arm robot.

Figure 3:
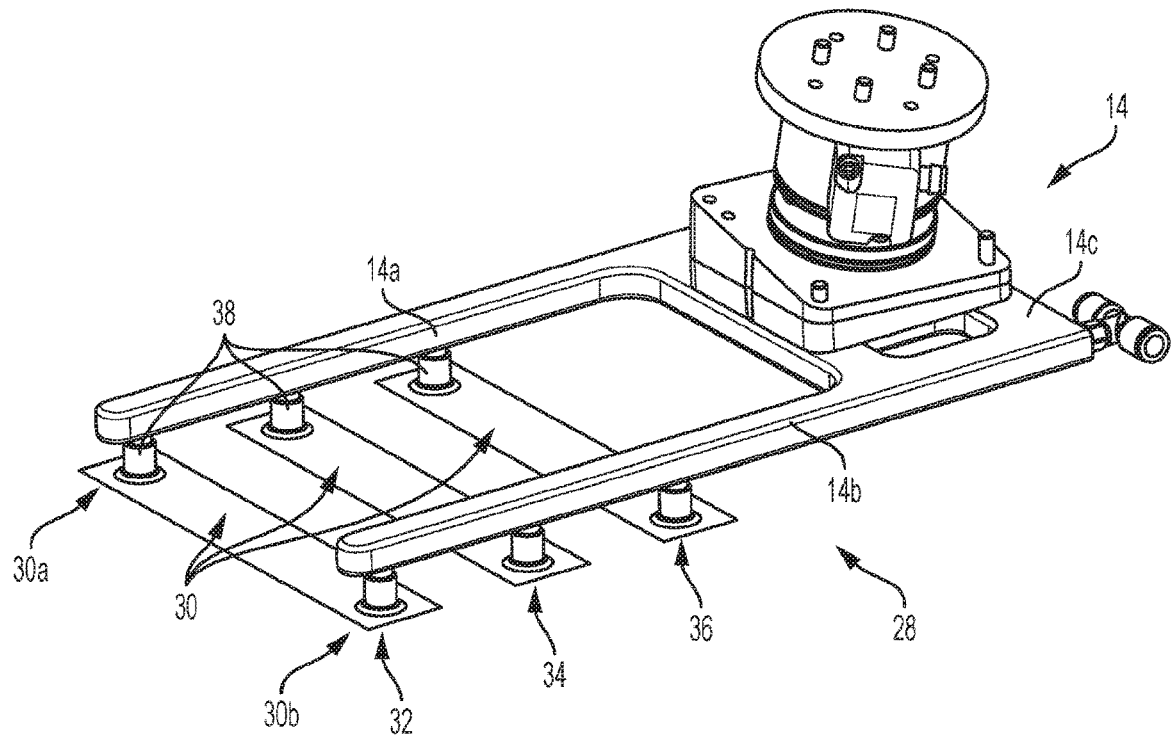
FIG. 3 shows a three-dimensional perspective view of a material holder system, according to an embodiment of the present disclosure.

FIG. 3 shows a three-dimensional perspective view of the material holder system 14, according to an embodiment of the present disclosure. The material holder system 14 is configured to hold and move the film sample being tested. The material holder system 14 may attach to the robotic system 12 with an adapter plate. The adapter plate may attach to an adapter plate on the robotic system 12. When attached, the adapter plate may transmit rotational, longitudinal, and angular motion from an articulating arm of the robotic system 12 to the material holder system 14. In an embodiment, the material holder system includes a vacuum suction system 28 adapted to hold the film sample (shown in FIG. 3 as three cut film specimens 30, as will be explained in more detail to follow) through vacuum suction. In an embodiment, the vacuum suction system 28 includes three sets 32, 34, 36 of vacuum cups 38. Each set may include two vacuum cups 38. This allows for the material holder system 14 to handle either a film sample of dimension 6"×6" (152 mm×152 mm), or three film specimens 30 of size 1"×6" (25 mm×152 mm) (e.g., which have been cut from the film sample). One of ordinary skill in the art will recognize that when a 6"×6" (152 mm×152 mm) film sample is handled by the material holder system 14, all six vacuum cups 38 can be employed to hold and move the film sample. When three film specimens of size 1"×6" (25 mm×152 mm) are handled by the material holder system 14, each set 32, 34, and 36 of vacuum cups 38 can hold and move a respective specimen. For example, the two vacuum cups 38 which make up set 32 can hold and move a single film specimen 30 of size 1"×6" (25 mm×152 mm) and likewise for each of sets 34 and 36. The material holder system 14 may hold and move the three specimens simultaneously. Although six vacuum cups 38 are described and shown, any number of vacuum cups may be used to hold and move the film through the testing process. For example, twelve vacuum cups 38 may be used such that six film specimens of size 1"×6" (25 mm×152 mm) are handled by the material holder system 14. One of ordinary skill in the art will appreciate that the tensile testing system 10 according to the present disclosure can be configured to test film samples having sizes other than 6"×6" (152 mm×152 mm), including non-square and non-rectilinear shapes. Additionally, one of ordinary skill in the art will appreciate that the tensile testing system 10 according to the present disclosure can be configured to cut and test film specimens having sizes other than 1"×6" (25 mm×152 mm), and in other shapes and quantities. Accordingly, the tensile testing system 10 is not limited to any particular size or shape of the film sample, or size, shape, and quantity of the specimens cut from the film sample.

Although vacuums cups are described herein as being used to hold the film, other mechanisms can also be used to hold the film, depending on the type of material. Vacuum cups may be well suited for holding non-porous and relatively light films, such as various plastics and polymer materials. Other holding mechanisms such as magnets, clips, or grippers may be suited for use with porous materials.

Still referring to FIG. 3, the material holder system 14 may comprise a generally u-shaped frame. The u-shaped frame may comprise two legs 14a, 14b, and a base 14c. The legs 14a, 14b may include the vacuum cups 38 and the base 14c may include the adapter plate for connection to the robotic system 12. The generally u-shaped frame allows for a vacuum cup 38 to be placed on each opposing end 30a, 30b of a film specimen 30, while allowing access to the film specimen between the vacuum cups 38. Although a generally u-shaped frame is depicted, the frame may take any shape which is able to support the film specimen 30 on opposing ends. Such alternative shapes could be generally v-shaped frames, square frames, c-shaped frames, etc.

Figure 4:
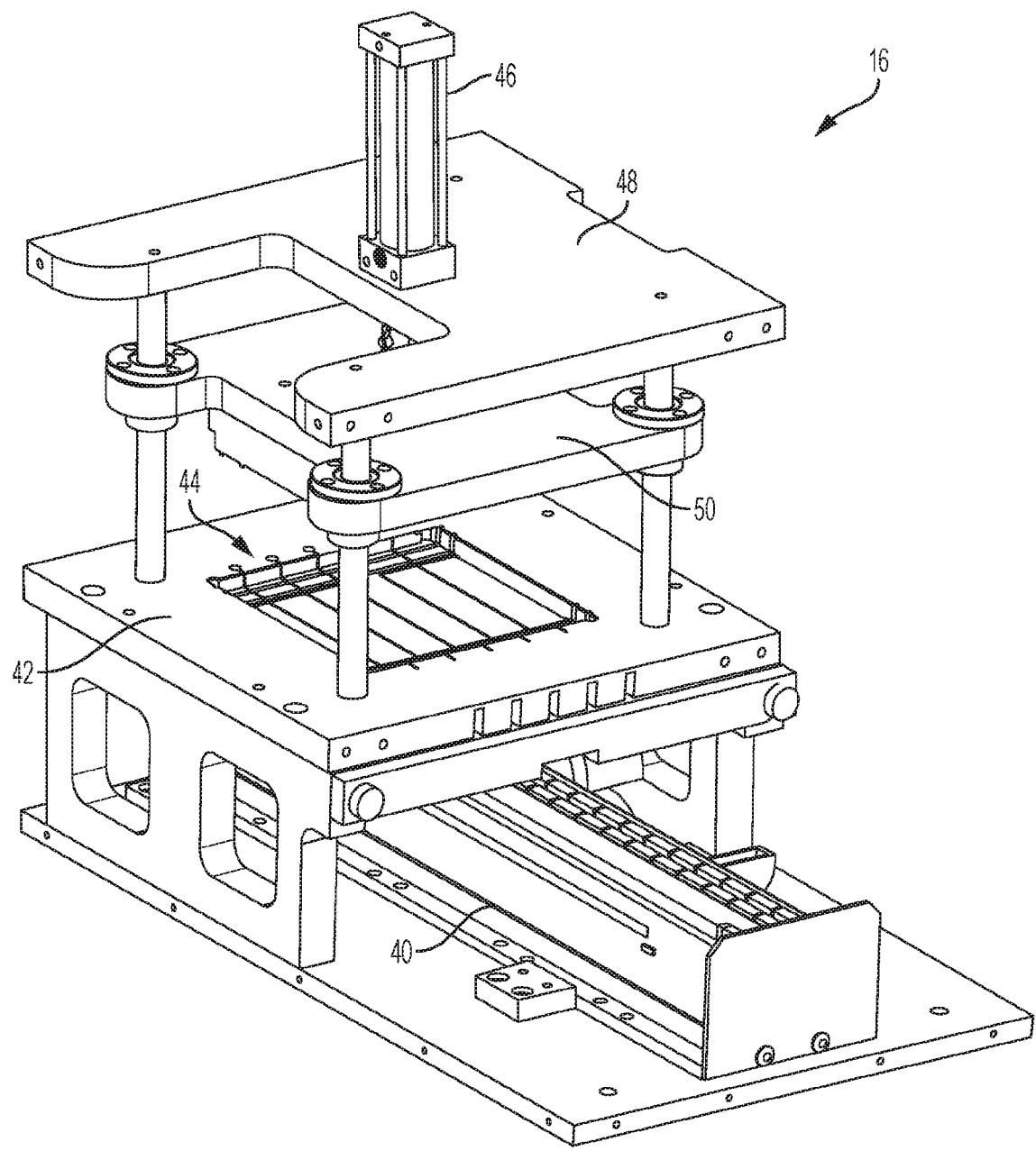
FIG. 4 shows a three-dimensional perspective view of a cutting device, according to an embodiment of the present disclosure.
Figure 5:
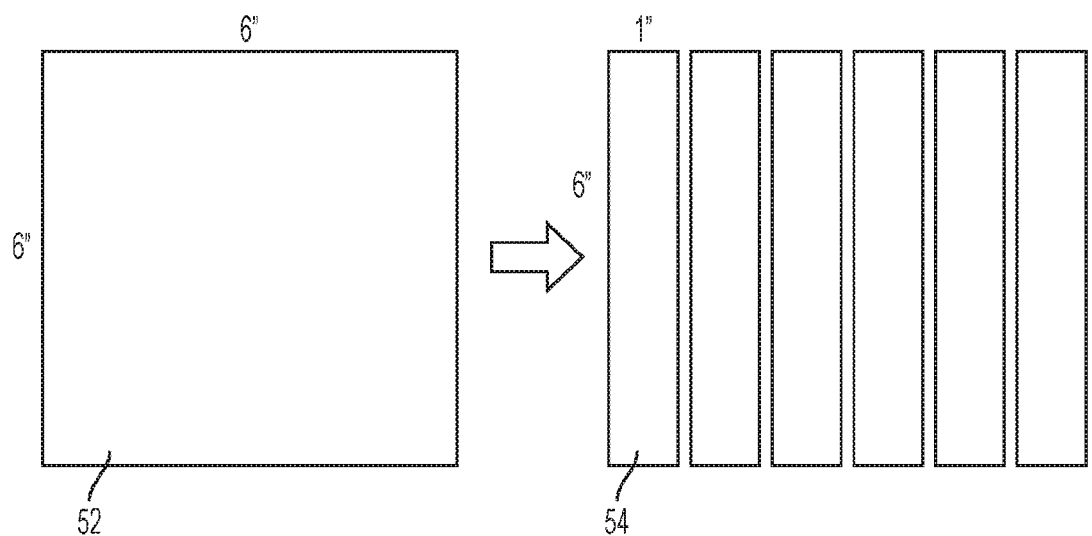
FIG. 5 shows a top view of a piece of film before and after being cut with a cutting device, according to an embodiment of the present disclosure.

FIG. 4 shows a three-dimensional perspective view of the cutting device 16, according to an embodiment of the present disclosure. For clarity of the description, the term "film sample" refers to a film material being tested in the tensile testing system 10 prior to the film material being cut with cutting device 16 and the term "film specimen" refers to the "film sample" which has been cut to a smaller size by the cutting device 16. The cutting device 16 is designed to cut a 6"×6" (152 mm×152 mm) square film sample 52 into six film specimens 54 each of size 1"×6" (25 mm×152 mm), as can be seen in FIG. 5. The cutting device 16 may include a linear actuator 40, such as a linear motor. The linear actuator 40 may drive five blades 56 (FIG. 6) to create five slits in the film sample. All five blades 56 may be actuated together to cut the film sample into six film specimens. Although an initial sample size of 6"×6" (152 mm×152 mm) and cut specimen size of 1"×6" (25 mm×152 mm) are disclosed, other dimensions are possible.

Figure 6:
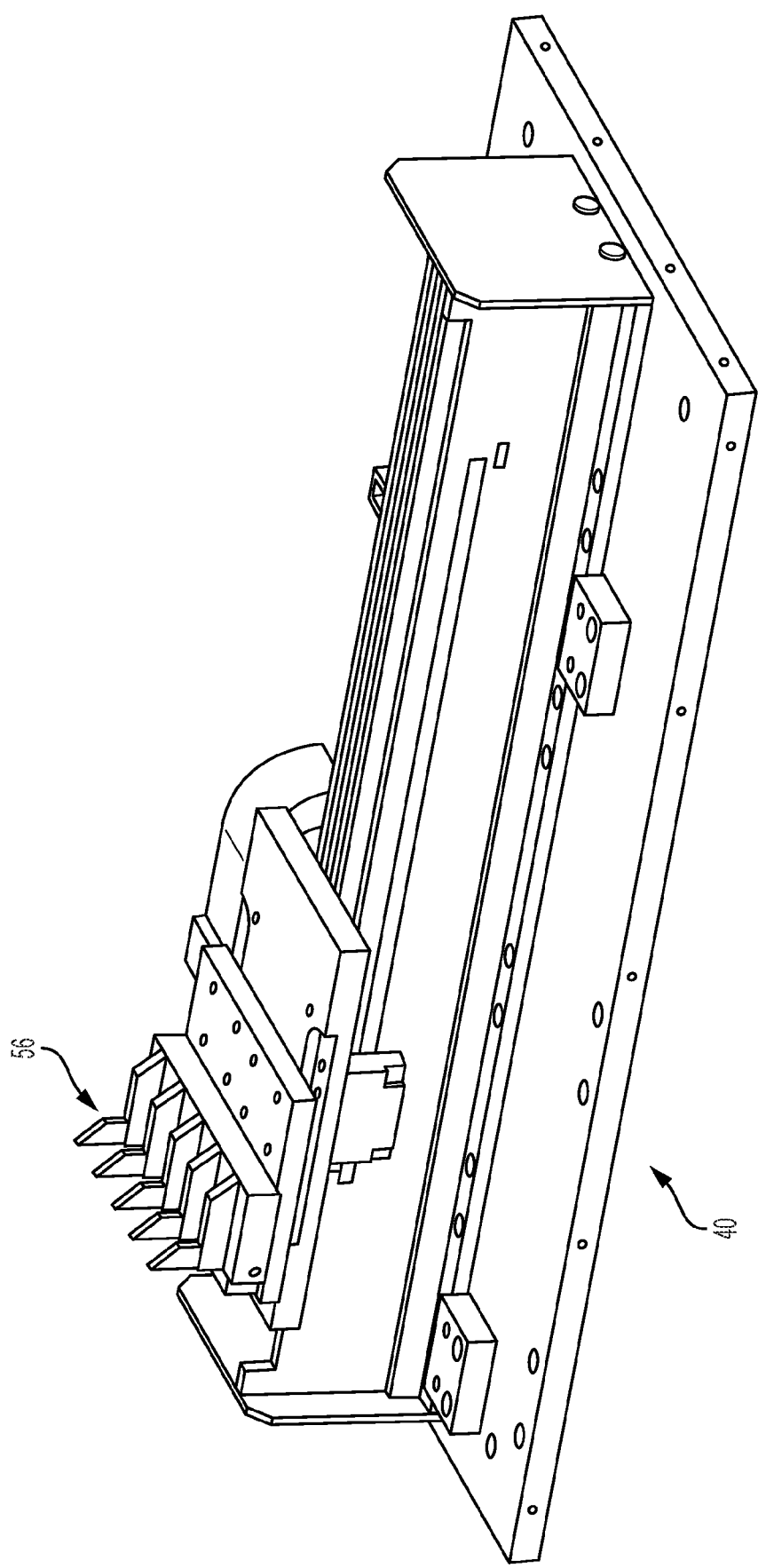
FIG. 6 shows a three-dimensional perspective view of components of a cutting device, according to an embodiment of the present disclosure.

Referring again to FIG. 4, the cutting device 16 may include a film support plate 42 defining a cavity 44. The cavity 44 may receive the 6"×6" (152 mm×152 mm) film sample 52. The cutting device 16 may also include a pneumatic cylinder 46 mounted to a mounting plate 48. The pneumatic cylinder 46 can be actuated to provide upward and downward motion to a pressure plate 50. In operation, the material holder system 14 places a 6"×6" (152 mm×152 mm) film sample 52 into the cavity 44, between the film support plate 42 and pressure plate 50, and the pressure plate 50 is lowered to maintain the film sample 52 in one position during cutting. Referring to FIGS. 4 and 6, the linear actuator 40 then moves the blades 56 to cut the film sample 52 into six film specimens 54.

Figure 7:
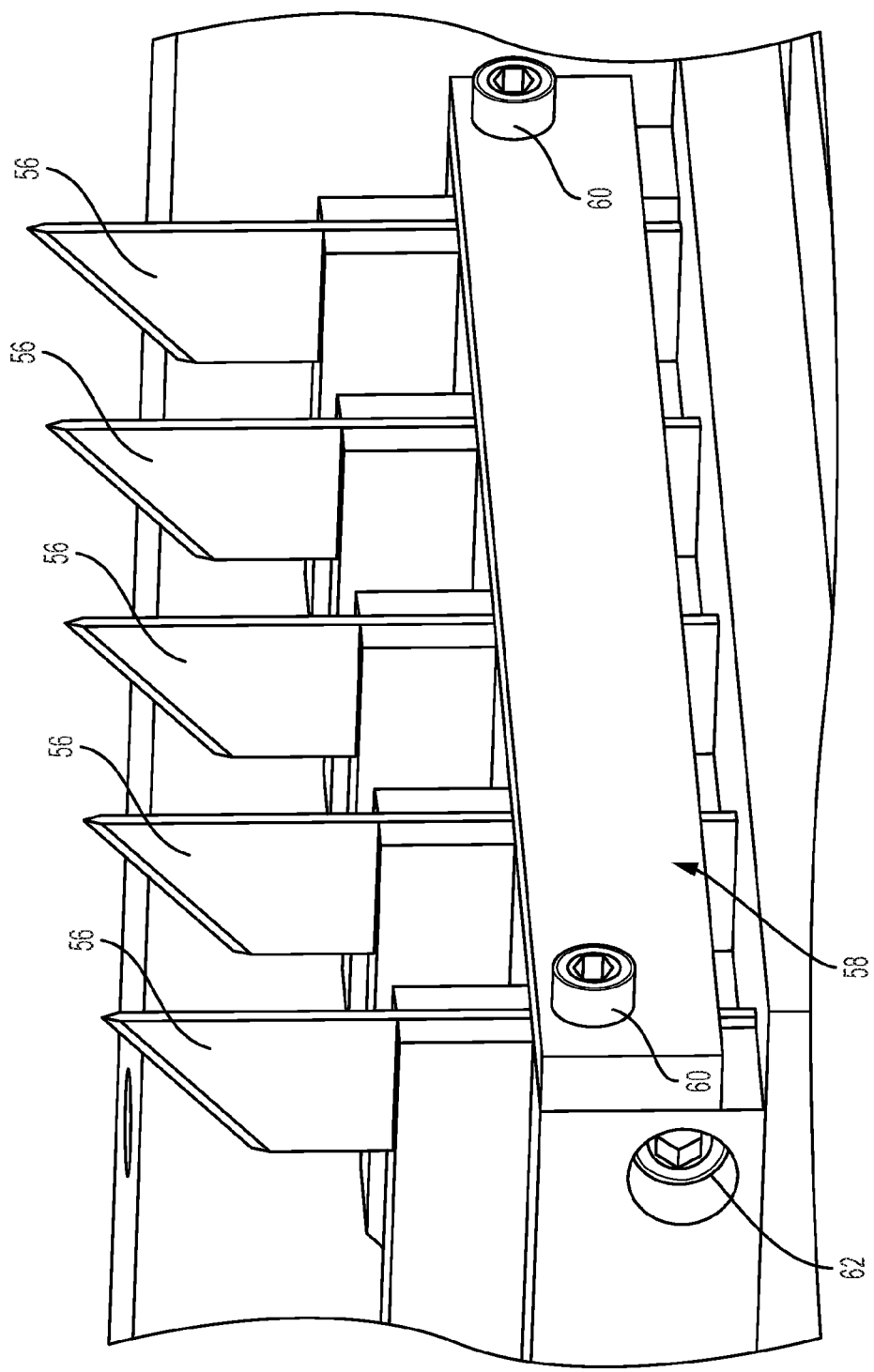
FIG. 7 shows a three-dimensional perspective view of components of a cutting device, according to an embodiment of the present disclosure.

As can be seen in FIG. 7, the blades 56 are secured by set bar 58 and screws 60. A bolt 62 runs through an aperture (not shown) in a lower portion of each blade 56. To remove the blade (such as for repair, cleaning, or replacement), the bolt 62 is removed and then blades 56 may be pulled upward and out of their respective slots.

Figure 8:
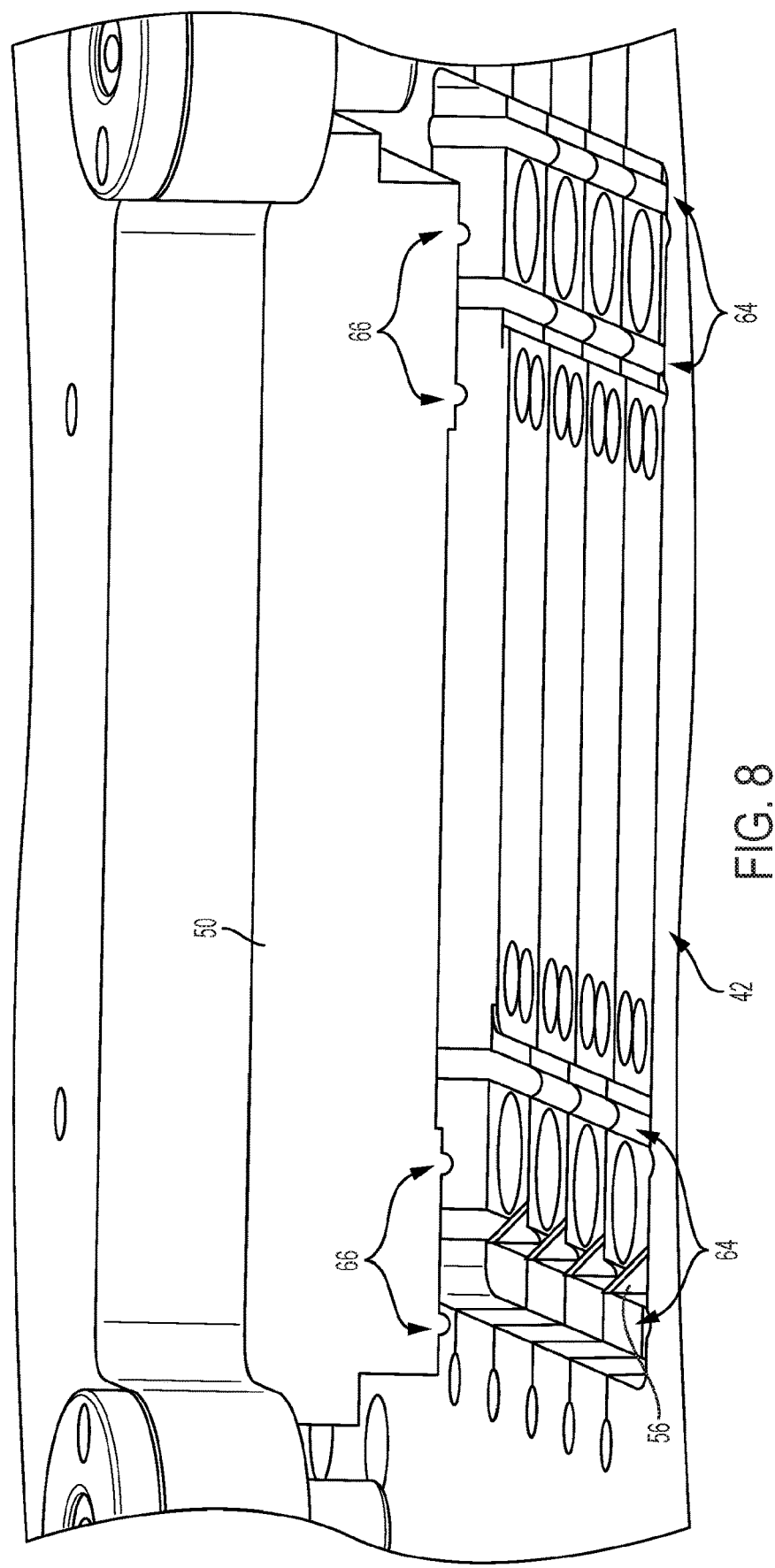
FIG. 8 shows a three-dimensional perspective view of components of a cutting device, according to an embodiment of the present disclosure.

FIG. 8 shows a three-dimensional perspective view of the film support plate 42 and pressure plate 50 of the cutting device 16, according to an embodiment of the present disclosure. Grooves 64 are milled into the film support plate 42 and tongues 66 are patterned into the pressure plate 50. The tongues 66 mate with the corresponding grooves 64 when the pressure plate 50 is against the film support plate 42 to hold the film sample into position while cutting. As can be seen in FIG. 8, the blades 56 may cut perpendicular to the tongue and groove pattern. According to an alternative embodiment, the grooves 64 may be located on the pressure plate 50 and the tongues 66 may be located on the film support plate 42.

Figure 9:
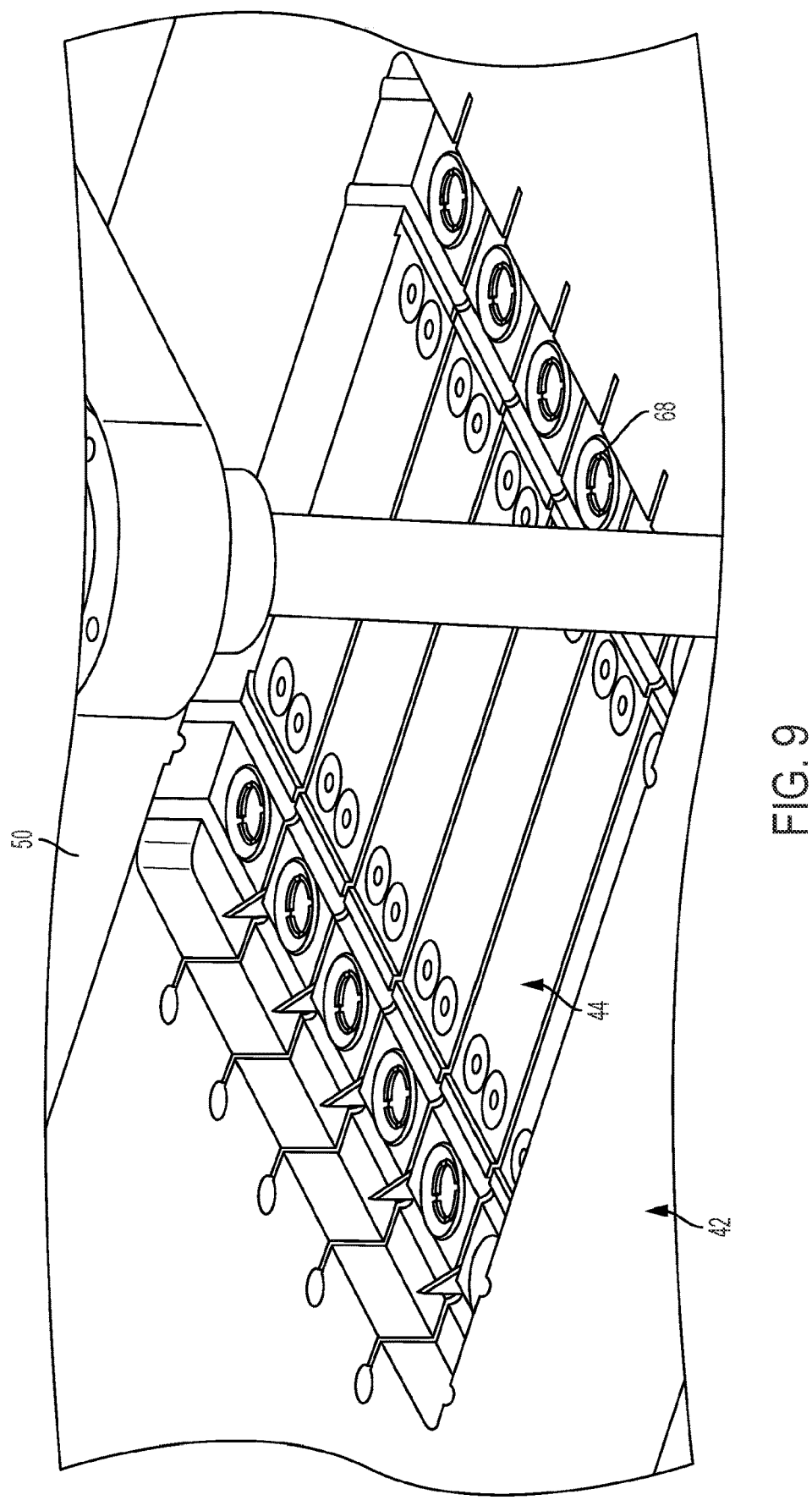
FIG. 9 shows a three-dimensional perspective view of components of a cutting device, according to an embodiment of the present disclosure.

FIG. 9 shows a three-dimensional perspective view of the film support plate 42 of the cutting device 16, according to an embodiment of the present disclosure. The film support plate 42 may include 12 vacuum cups 68 divided into six sets. After cutting, the vacuum cups 68 hold the six film specimens in place while the pressure plate 50 begins to rise. The film specimens then stay in place while the pressure plate 50 is moved upward by the pneumatic cylinder 46. Alternative cutting devices may be employed. For example, the cutting device may be a cutting wheel, laser cutter, die cutter, or rolling drum die.

Following cutting, the film specimens may be moved by the robotic system 12 and material holder system 14 to the material image analyzer system 18. Although the process is described with material image analysis following cutting, it will be recognized that the order may be altered, for example, based on proximity of the component on the work surface 24 to promote efficiency of the system. Thus, the film may be moved to the material thickness measurement system 20 after cutting or alternatively, the film may be moved to either or both of the material image analyzer system 18 and material thickness measurement system 20 prior to cutting with the cutting device 16.

The material holder system 14 may be constructed with vacuum cups 38 to move three film specimens from the cutting device 16 at a time. For example, the material holder system 14 may lift every other film specimen, that is the first, third, and fifth film specimens, and move them to the subsequent stations (e.g., tensile testing apparatus 22). Alternatively, the material holder system 14 may be constructed with additional vacuum cups 38 such that the material holder system 14 may lift all six film specimens at the same time and move them to the subsequent stations (e.g., tensile testing apparatus 22).

Figure 10:
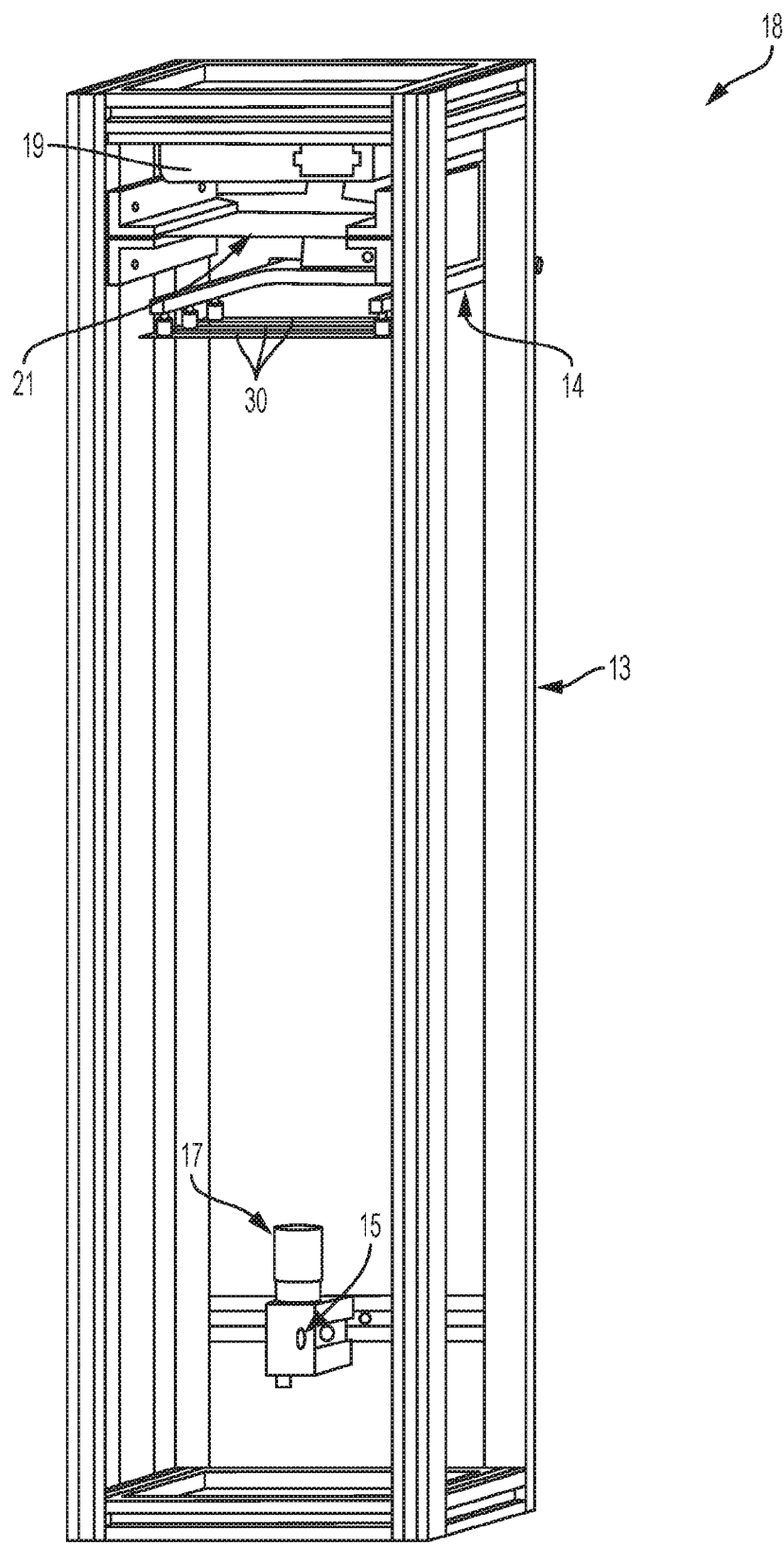
FIG. 10 shows a three-dimensional perspective view of components of a material image analyzer system, according to an embodiment of the present disclosure.

The robotic system 12 and material holder system 14 may transport the film sample or film specimens to the material image analyzer system 18, shown in FIG. 10. The material image analyzer system 18 may examine the film sample or cut film specimens 30 for irregularities and potential defects. The material image analyzer system 18 may detect a film region which does not contain defects that will affect results, edges of the film (e.g., if the edges of the film are jagged), and/or that the film is held squarely (i.e. properly oriented) in the material holder system 14. Additionally or alternatively, the material image analyzer system 18 may detect the width of the film sample or each of the cut film specimens 30.

The material image analyzer 18 may include a frame 13 that houses a light source 19 of polarized light, a polarizing film 21, a camera 15, and a polarizing filter 17 placed onto a lens of the camera 15. The light source 19 of polarized light is used to illuminate the film specimens 30 (or film sample) within the material image analyzer system 18, while eliminating any ambient light through the polarizing film 21. After the light passes through the film specimens 30 (or film sample), it is captured by the camera 15 fitted with the polarizing filter 17. A perfectly formed piece of film does not scatter the polarized light from the light source 19 thus resulting in a completely clear image. However, any imperfections or defects in the film scatter light that is detected by the camera 15. A machine vision algorithm then identifies and tags film with significant defects. Therefore, the material image analyzer system 18 is based on detecting irregularities caused when polarized light passing through the film is affected by certain physical defects. Because the material image analyzer system 18 relies on polarization of light, when the material to be tested is changed, the polarization may also change which would potentially indicate a defect to be present where there is none. However, as part of the analysis aspect, defect or irregularity analysis can be shifted to the data interpretation and conducted by looking at the range of results from a material specimen and identifying outliers based on standard deviation and distance from the mean. Therefore, the present method of determining defects can operate independent of the material, and can provide a more universal application. Alternative image analyzers may be employed, such as gel testers that quantitate and identify the types of defects, for example, optical control systems.

The material image analyzer system 18 may also detect a width of the film sample or film specimens 30. The robotic system 12 may move the material holder system 14 and film specimens 30 between the polarizing film 21 and the camera 15. The film sample or film specimens 30 may be imaged between the polarizing film 21 and the polarizing filter 17. The film sample or film specimens 30 may have a grain structure that polarizes light in a specific orientation. The image produced may be a direct representation of the granular structure of the film. The image may then be binarized to black and white, resulting in the film sample or film specimens 30 appearing as solid white. The right and left edges of the film sample or film specimens 30 may be detected at three separate locations along the length of the film sample or film specimens 30. The edge detection may be performed, for example, with three sets of Epson vision edge objects. The vision edge objects may locate a pixel at each of the three locations along the length, at each of the left side and right side where the image transitions from black to white. The number of pixels between the respective left side and the right side at each of the three locations may be calculated. This may result in a width determination at each of the three locations along the length of the film sample or each film specimen 30. The three width determinations or distances may be averaged and converted from pixels per inch to inch. This may result in a width determination for the film sample or for each of the film specimens 30.

The camera 15 may be a high-resolution camera with a 25 mm (1") lens having the polarizing filter 17 attached thereto. The 25 mm lens may provide a focal length of approximately 20 inches (508 mm) from the surface of the lens. The light source 19 may be a four inch (100 mm) square light. The polarizing film 21 may be mounted about one inch (25 mm) below the light source 19. The polarizing film 21 and the polarizing filter 17 on the camera 15 may be rotated 90-degrees in relation to each other. The 90-degree relationship may prevent light leaving the light source 19 from reaching the camera 15 if no object (e.g. no film sample or no film specimen 30) is between the polarizing filter 17 of the camera 15 and the polarizing film 21.

Figure 11:
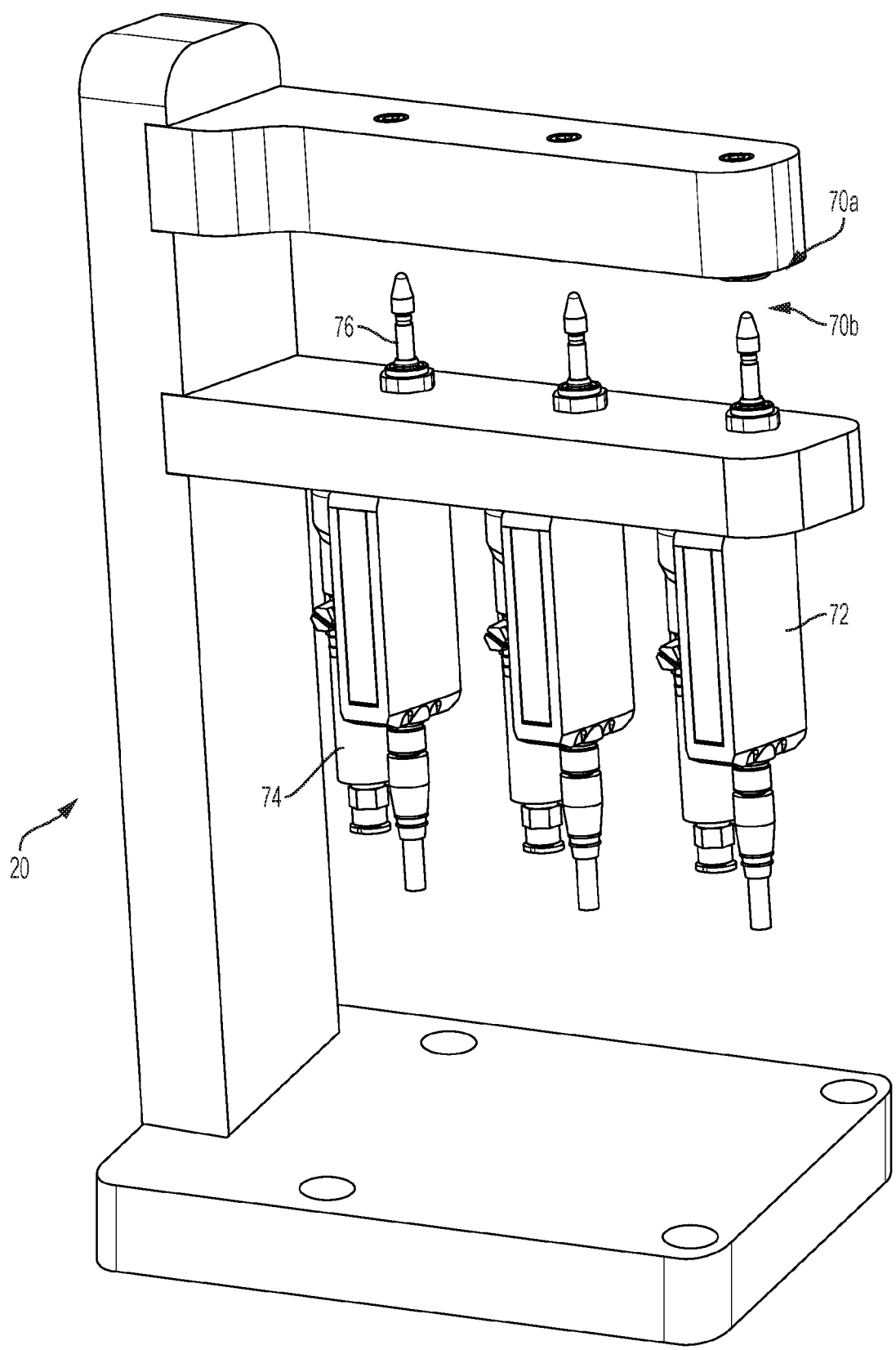
FIG. 11 shows a three-dimensional perspective view of components of a thickness measurement system, according to an embodiment of the present disclosure.

Referring to FIG. 11, the robotic system 12 and material holder system 14 may transport the film specimen to the material thickness measurement system 20. For example, this may occur after analysis by the material image analyzer system 18. Alternatively, this may occur at another stage in the process. FIG. 11 shows a three-dimensional perspective view of the components of the material thickness measurement system 20, according to an embodiment of the present disclosure. The material thickness measurement system 20 is configured to measure a thickness of the film specimen in a wide range of thicknesses, for example between 0.5 mil to 10 mil (0.0127 mm to 0.254 mm). The material thickness measurement system 20 is configured to measure a thickness of the film specimen over a certain surface area by using contact surfaces 70a, 70b. The thickness measurement system 18 is configured to measure a thickness of the film using a contact plate and a probe. The contact plate and the probe are generally flat and contact the film on opposing surfaces 70a and 70b, respectively, and the thickness of the film is measured as the distance between the contact plate and the probe. The surface 70a of the contact plate and the surface 70b of the probe is sufficient to avoid puncturing the film sample during the measurement. For example, the contact surfaces 70a, 70b can be configured to be used for materials that are flexible and pliable. The contact surfaces 70a, 70b can also be configured to measure a thickness of more rigid samples. As can be seen in FIG. 11, the material thickness measurement system 20 may comprise three upper contact surfaces 70a and three lower contact surfaces 70b and three sensors 72 to measure the thickness in an area which corresponds to each of three film specimens. The 1"×6" (25 mm×152 mm) film specimens are inserted between the contact surfaces 70a, 70b and the thickness is measured at a point in each sample. The material thickness measurement system 20 may measure the thickness of the film specimen in a location prescribed by ASTM D882. Alternatively, the material thickness measurement system 20 may comprise six of each of contact surfaces 70a, 70b and six sensors 72 to accommodate the thickness testing of six film specimens simultaneously or substantially simultaneously. The film measurement system may alternatively measure three or six locations on the uncut film sample prior to cutting by the cutting device. In this embodiment, the measured locations may correspond to locations on the cut film specimens, once cut.

According to the embodiment shown, the material thickness measurement system 20 also includes digital contact sensors 72 (for example, Keyence GT2 Series from Keyence Company). The sensors 72 can be used to measure the thickness of the film specimen to an accuracy of 1 micron. The contact surface 70b is mechanically linked to the sensor 72 by shaft 76. The robotic system 12 and material holder system 14 locate the film specimen in place between the contact surfaces 70a, 70b. Once the film specimen is in place between contact surfaces 70a, 70b, pressurized air from air-pressure systems 74 is applied to the sensors 72 that extends a shaft 76 linked to sensor 72 to move the contact surface 70b upward. The film specimen may be held between the contact surfaces 70a, 70b. The sensor 72 may measure the distance between the extended contact surface 70b and the upper contact surface 70a to measure the thickness of the film specimen.

Although a mechanical type material thickness measurement system 20 is described and used, as it must be appreciated other types of thickness measuring systems can also be employed. For example, in another embodiment, the material thickness measurement system 20 includes laser distance measuring sensors adapted to determine the thickness using laser beams. Alternatively, confocal lens, dual laser thickness analyzers, and capacitive measurement methods may be used to measure the thickness of the film specimens.

Figure 12:
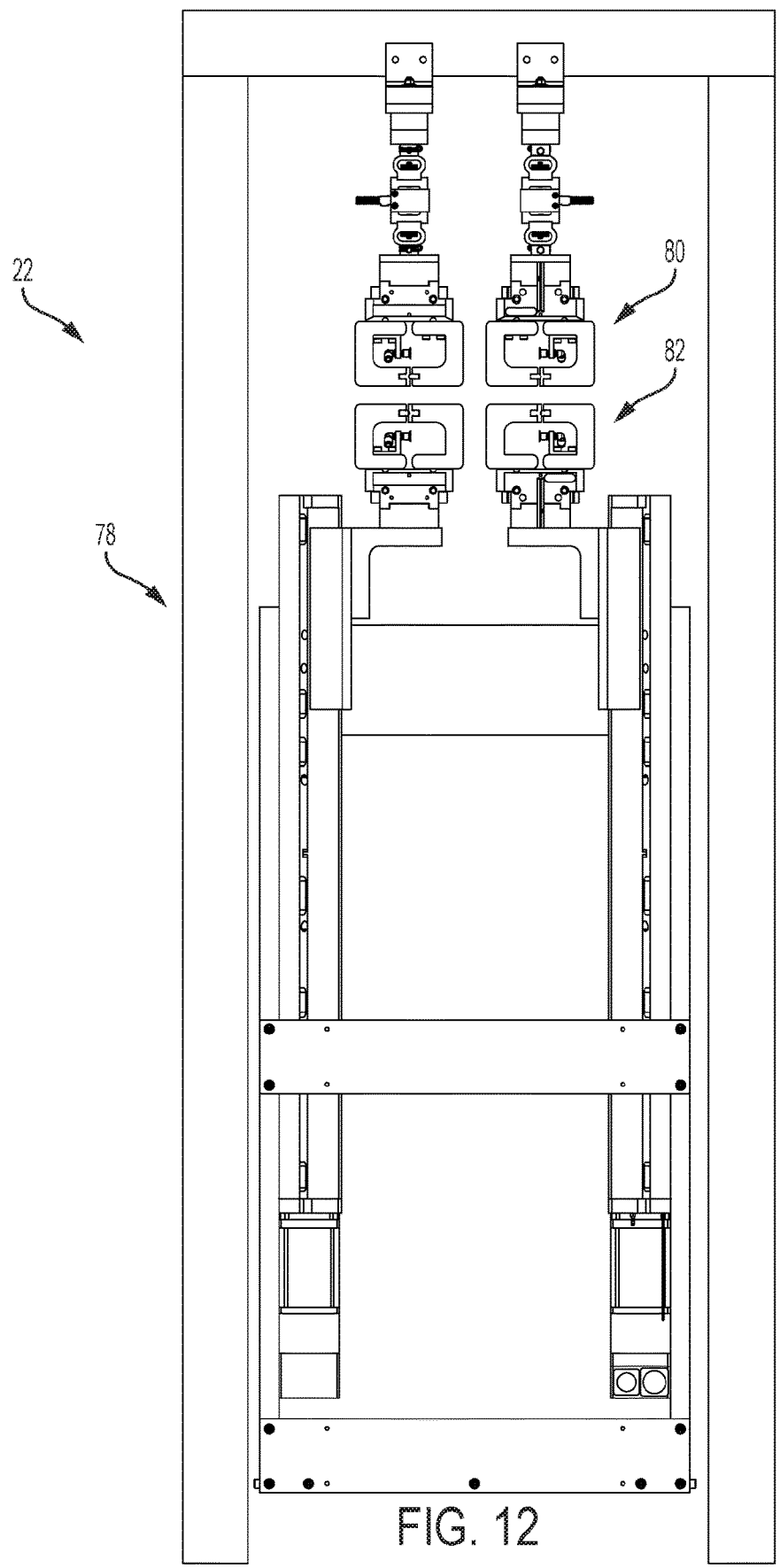
FIG. 12 is a front view of a tensile testing apparatus, according to an embodiment of the present disclosure.

Referring to FIG. 12, the robotic system 12 and material holder system 14 may transport the film specimen to the tensile testing apparatus 22. For example, this may occur after analysis by the material thickness measurement system 20. Alternatively, this may occur at another stage in the process. FIG. 12 shows a front view of the tensile testing apparatus 22, according to an embodiment of the present disclosure. The tensile testing apparatus 22 may include a frame 78 having an upper gripper 80 and a lower gripper 82.

Figure 13:
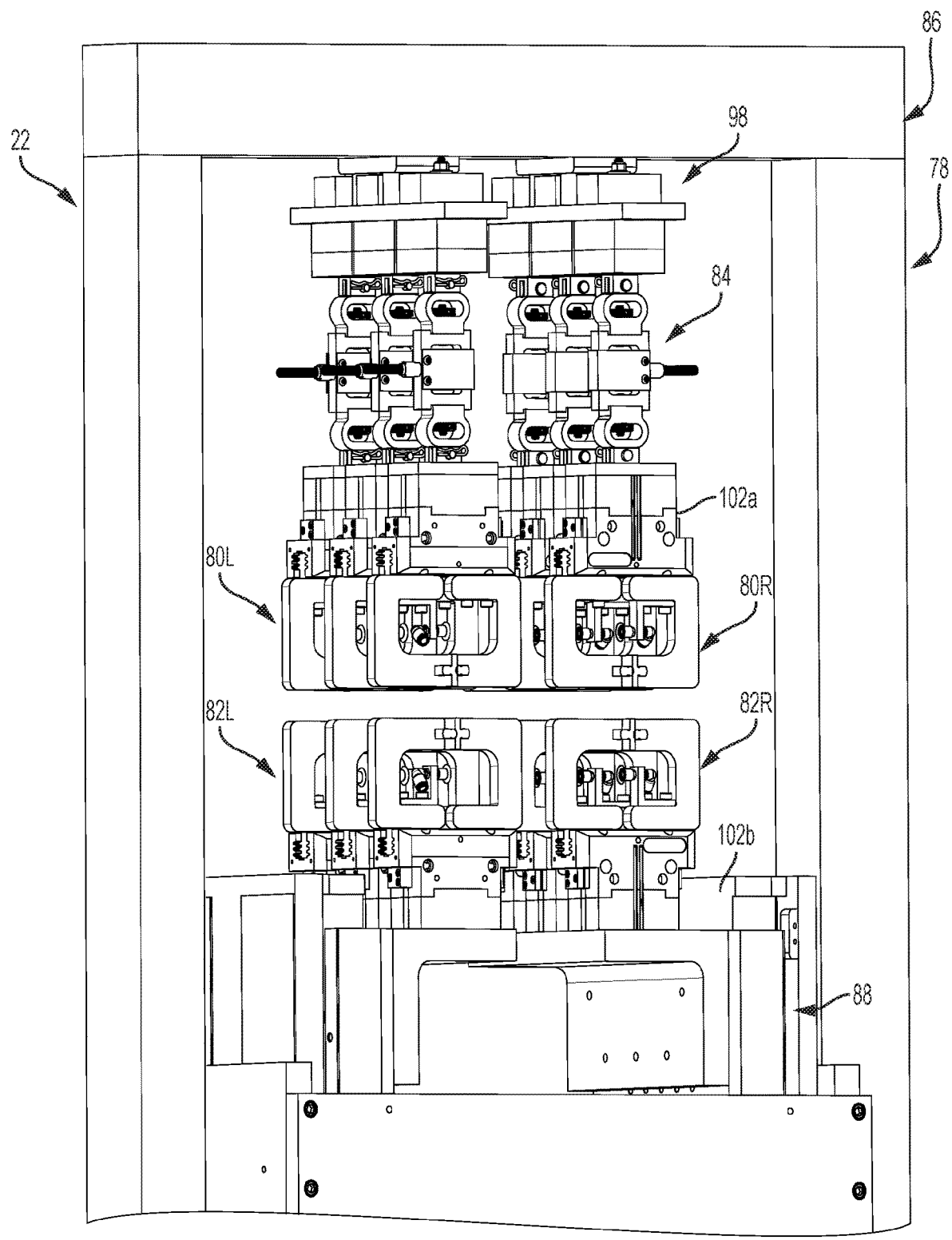
FIG. 13 shows a three-dimensional perspective view of components of a tensile testing apparatus, according to an embodiment of the present disclosure.

FIG. 13 shows a three-dimensional perspective view of an upper portion of the tensile testing apparatus 22, according to an embodiment of the present disclosure. The upper gripper 80 and lower gripper 82 are selected so as to exert force on the film specimen to prevent slippage of the sample during the tensile test. An exemplary gripper may be the Schunk PGN+100-1-AS pneumatic gripper. As depicted in FIG. 13, the tensile testing apparatus can comprise six upper grippers 80 and six lower grippers 82 arranged in sets to accommodate six tensile tests simultaneously, substantially simultaneously, or overlapping in time. The six tensile tests may also be performed in a sequential manner. Fewer or less than six sets of grippers are also possible, depending on the quantity of film specimens to be tested.

With continued reference to FIG. 13, the tensile testing apparatus 22 also includes a load cell 84 for each set of grippers. In the embodiment depicted, the load cell 84 is mounted to the upper gripper 80, but other mounting locations are possible. The load cell may be a Futek load cell. The load cells may be chosen to have a fast refresh rate and a high resolution. In an embodiment, the load cells may have a refresh rate of about 5100 Hz. In an embodiment, the load cells may have a resolution of about 0.025 lbf. The load cell 84 may be any load cell able to achieve accurate results with a fast refresh rate to achieve high throughput testing. The load cell 84 may be any load cell strong enough to handle a wide range of films and materials. The load cell 84 may be any load cell which exhibits linearity with other load cells. The load cell may be an Instron branded load cell.

Figure 17:
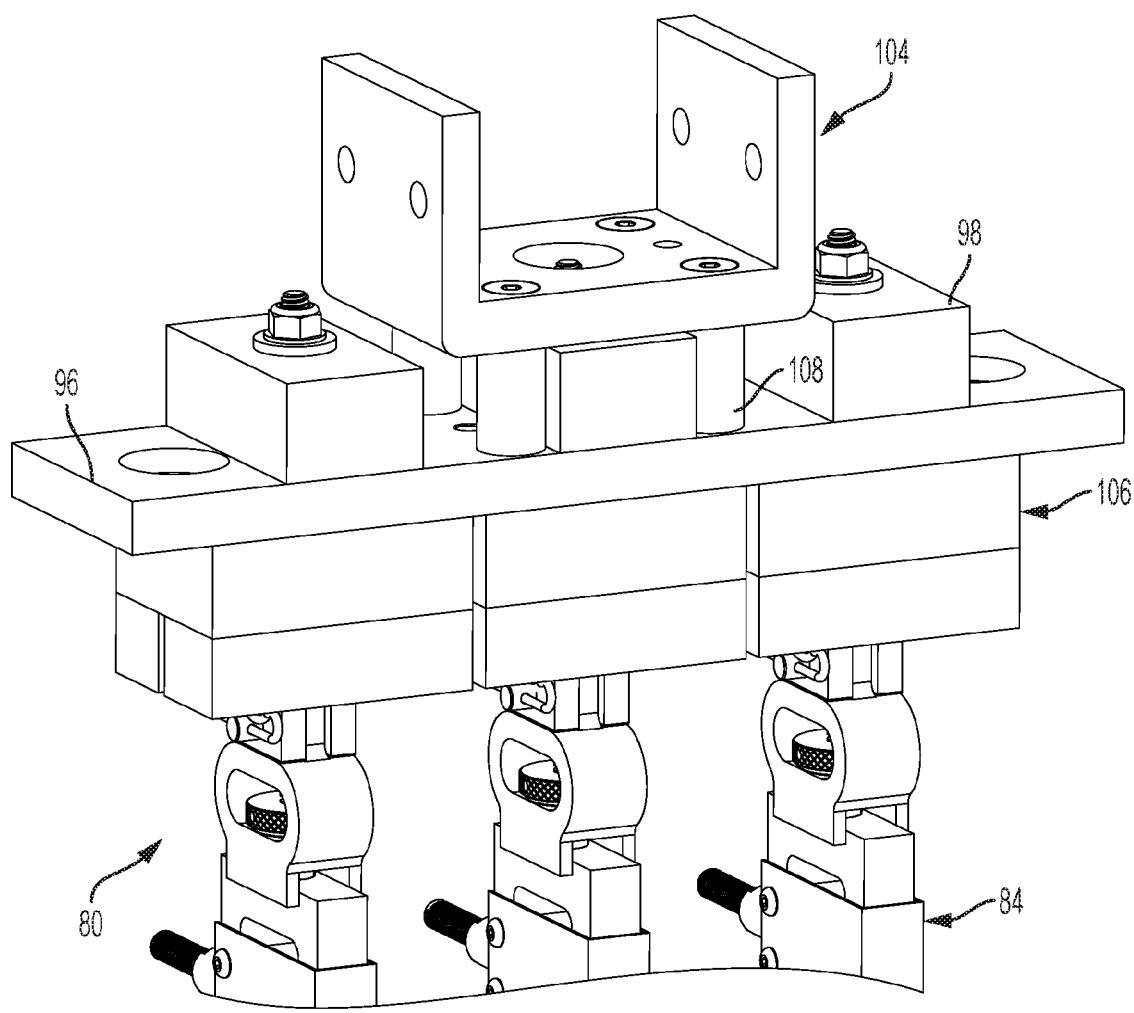
FIG. 17 shows a three-dimensional perspective view of components of a tensile testing apparatus, according to an embodiment of the present disclosure.

Referring again to FIG. 13, the frame 78 of the tensile testing apparatus 22 may include an upper frame 86 and a lower frame 88. The upper frame 86 may be stationary and hold the upper grippers 80. Each upper gripper may be attached to the upper frame 86 by mounting block 102a, load cell 84, and load mount 98 (FIG. 17). The load mount 98 may be attached to the upper frame 86 with a bracket 104 (FIG. 17). The bracket 104 may be u-shaped. The bracket 104 may be connected to the upper frame 86 in a manner known in the art, such as with fasteners. The lower frame 88 may hold the lower grippers 82. Each lower gripper 82 may be attached to the lower frame 88 by a mounting block 102a, 102b. The mounting blocks 102a and 102b may be any structure which allows connection of the grippers 80 and 82, respectively, to the upper frame 86 and lower frame 88, respectively. The upper grippers 80 and lower grippers 82 may be arranged with a set of three each of the upper grippers 80 and lower grippers 82 on a first side of the frame 78 (i.e. the set of grippers 80L and 82L). A second set of three each of the upper grippers 80 and lower grippers 82 may be present on a second side of the frame 78 (i.e. the set of grippers 80R and 82R). Although each set 80L/82L and 80R/82R are depicted as comprising three sets of upper grippers 80 and lower grippers 82, it is understood that more or fewer sets of grippers may be provided.

During a tensile test, the film specimen 54 may be gripped in an upper gripper 80 and a lower gripper 82. The lower frame 88 may be actuated to move in a downward direction while the upper frame 86 remains stationary, thus stretching the film specimen 54. As will be understood from the present disclosure "downward" refers to a direction relative to the upper grippers 80 and lower grippers 82. The tensile testing apparatus 22 may be operated in an orientation relative to gravity. The lower frame 88 can be actuated to move with a linear actuator, motor, or other device able to move the lower frame 88 at a predetermined speed. The lower frame 88 can move at a constant speed, or alternatively, a variable speed. When the test is completed, the lower frame 88 may be actuated (e.g. by the linear actuator) to return to the starting position. Although the tensile testing apparatus 22 is described with the upper frame 86 remaining stationary and the lower frame 88 moving, according to an alternative embodiment, the upper frame 86 may be the moveable while the lower frame 88 remains stationary. Alternatively, both the upper frame 86 and lower frame 88 may be moveable, through use of an actuator (e.g. a linear actuator) attached to both the upper frame 86 and lower frame 88, in opposing directions to stretch a film specimen 54.

Figure 14:
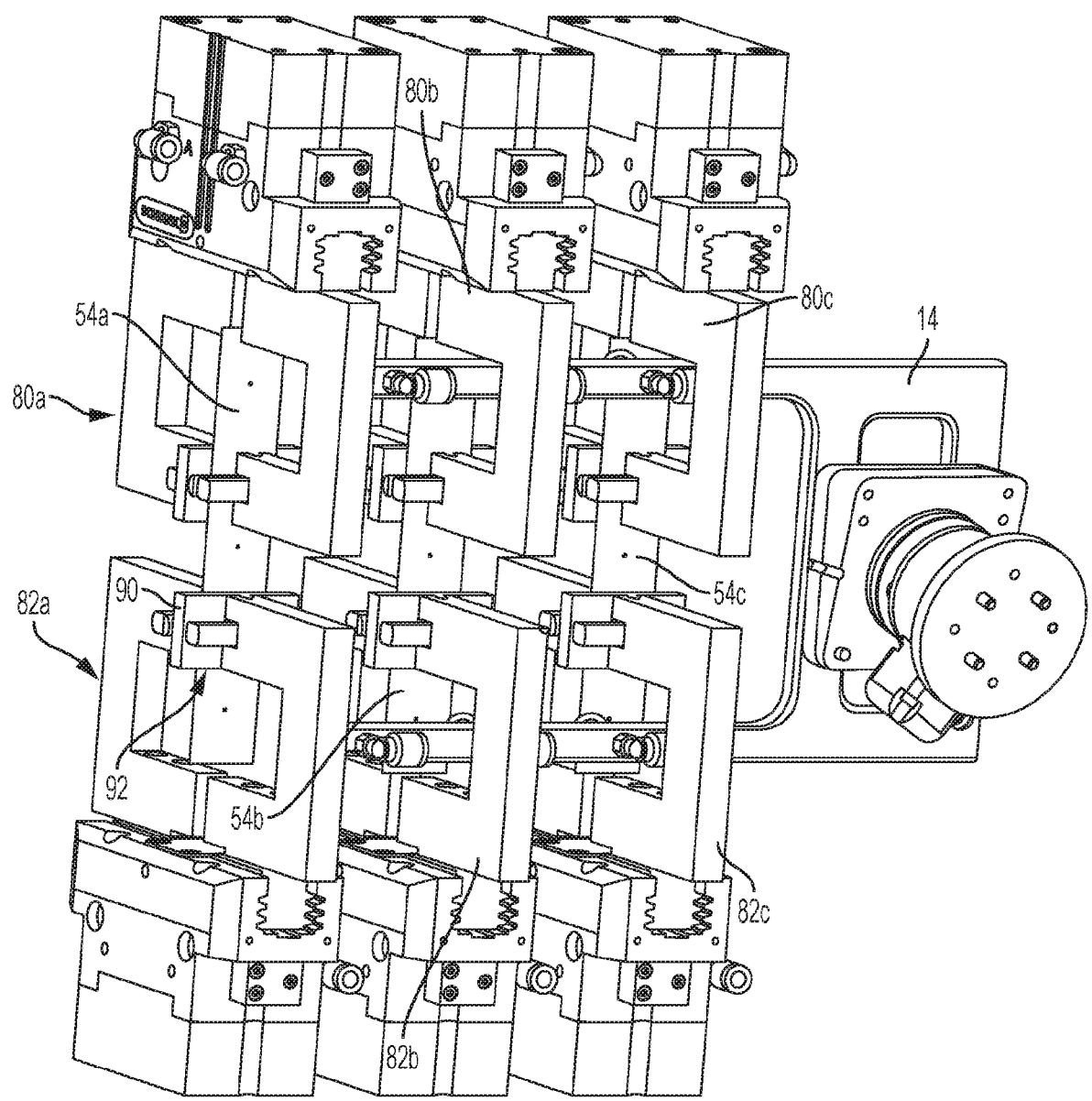
FIG. 14 shows a three-dimensional perspective view of a material holder system located in between grippers of a tensile testing apparatus, according to an embodiment of the present disclosure.
Figure 15A:
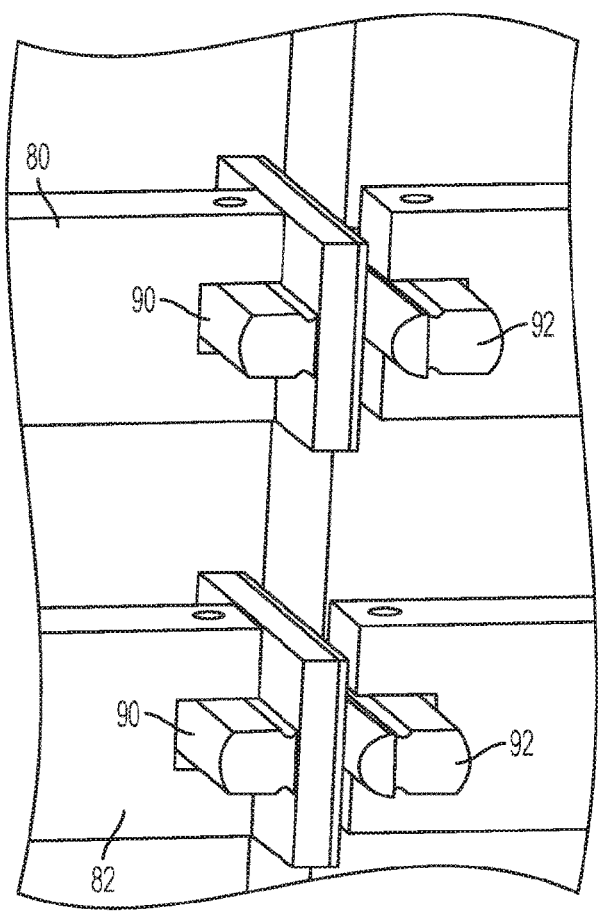
FIGS. 15A and 15B show a three-dimensional perspective view of placement of gripper faces on a gripper of a tensile testing apparatus, according to an embodiment of the present disclosure.
Figure 15B:
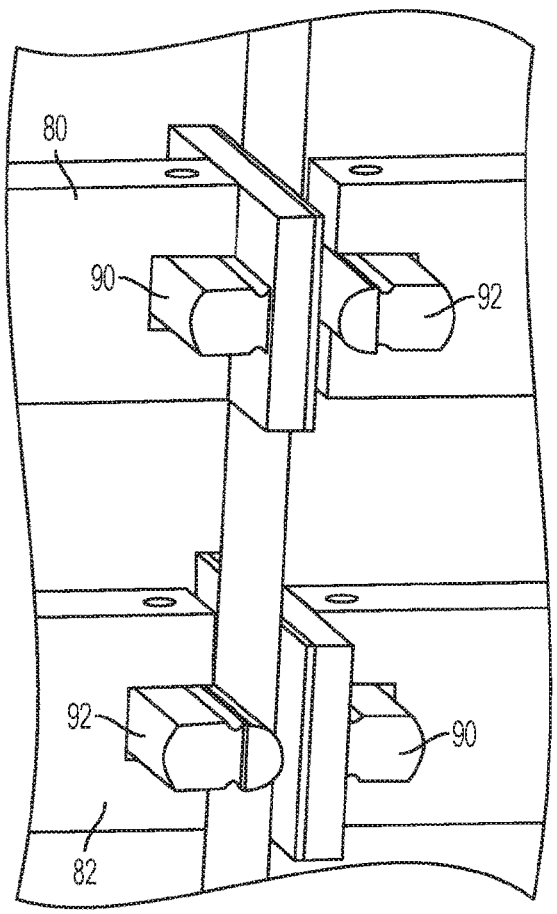

FIG. 14 shows a three-dimensional perspective view of the upper gripper 80 and lower gripper 82, according to an embodiment of the present disclosure. In FIG. 14, the material holder system 14 can be seen placing three film specimens 54 between the respective sets of upper grippers 80 and lower grippers 82. As depicted, the film specimens are held by the material holder system 14. The material holder system 14 may be moved by the robotic system 12 to the location depicted in FIG. 14. The film specimens 54a, 54b, 54c may be aligned with their respective pair of upper grippers 80a, 80b, 80c and lower grippers 82a, 82b, 82c. That is, a first film specimen 54a is located between a first upper gripper 80a and a first lower gripper 82a. A second film specimen 54b is located between a second upper gripper 80b and a second lower gripper 82b. A third film specimen 54c is located between a third upper gripper 80c and a third lower gripper 82c. The grippers may be actuated by a pneumatic operator to hold the samples in place with line grips 90, 92 (FIG. 15A, 15B). After placement of the specimens, the vacuum cups 38 on the material holder system 14 may be released from the film specimens and the material holder system 14 may be retracted from the grippers, and the testing may proceed. Although three film specimens are depicted as held by the material holder system 14 and grippers 80, 82, it is understood that more or fewer film specimens and upper grippers 80 and lower grippers 82 may be used.

According to an alternative sequence of operation, the material holder system 14 aligns a first film specimen 54a with a first set of upper and lower grippers 80a, 82a. The pneumatic operator actuates the grippers 80a, 82a to close. The vacuum cups 38 on the material holder system 14 are released only from the gripped specimen 54a. The material holder system 14 may then be moved to align a second film specimen 54b with a second set of upper and lower grippers 80b, 82b. The pneumatic operator actuates the second set of grippers 80b, 82b to close. The vacuum cups 38 on the material holder system are released only from the second gripped specimen 54b. The material holder system 14 may then be moved to align a third specimen 54c with a third set of upper and lower grippers 80c, 82c. The pneumatic operator actuates the third set of grippers 80c, 82c to close. The vacuum cups 38 are released only from the third gripped specimen 54c. The material holder system 14 is retracted from the grippers and testing may proceed. Thus, according to this embodiment, the three film specimens are placed in the tensile testing apparatus 22 in a sequential manner.

Although the material holder system 14 is depicted as placing three film specimens 54a, 54b, 54c in three sets of upper grippers 80a, 80b, 80c and lower grippers 82a, 82b, 82c; the material holder system 14 may alternatively hold all six film specimens 54 (cut from film sample 52, see FIG. 5) simultaneously. That is, the material holder system 14 may include six sets of vacuum cups 38 (FIG. 3) able to hold six film specimens 54. According to this embodiment, the material holder system 14 may deliver three of the film specimens 54 to three sets of grippers (e.g. 80L, 82L in FIG. 13). After placement of the first three film specimens 54, in one of the manners previously described, the material holder system 14 may deliver the remaining three film specimens 54 to a three sets of grippers (e.g. 80R, 82R in FIG. 13), in a manner previously described. In this manner, testing on the first three film specimens may proceed while the material holder system 14 delivers the remaining three film specimens to the tensile testing apparatus 22. Alternatively, all six film specimens may be tested simultaneously. Alternatively, more or less than six film specimens may be placed and tested in the aforementioned manners.

FIGS. 15A and 15B show three-dimensional perspective views of upper gripper 80 and lower gripper 82. Each upper gripper 80 may comprise line grips 90, 92. Each lower gripper 82 may similarly comprise line grips 90, 92. Line grips 90, 92 may hold the samples in place during testing. The upper and lower grippers 80, 82 in combination with the line grips 90, 92 ensure the proper force is applied to the film specimen during test. Too little force may cause slippage of the film specimen and too much force may cause premature breaking or pinching of the film specimen.

As shown in FIGS. 15A and 15B, orientation of the faces of line grips 90, 92 does not affect the ability of the grippers 80, 82 to hold the film specimen during test. Line grips 90 are depicted as having a substantially planar face. Line grips 92 are depicted as having a substantially curved face. Line grips 90 and 92 may be placed on upper gripper 80 and lower gripper 82 such that both line grips 90 with planar faces are located on the same side of upper gripper 80 and lower gripper 82 (as seen in FIG. 15A). Similarly, both line grips 92 with curved faces can be located on the opposing side of line grips 90 on both upper gripper 80 and lower gripper 82. Alternatively, the upper gripper 80 may have a line grip 90 with a planar face on the same side as a line grip 92 with curved face on lower gripper 82 (as seen in FIG. 15B). Alternatively, the upper grippers 80 and lower grippers 82 may be other types of grips suitable for holding a material sample, such as, for example, flat-faced grips, rubber coated grips, texturized grips, etc.

The tensile testing system 10 may test multiple film specimens in parallel, or substantially in parallel. For example, in use, the material holder system 14 may place three film specimens 54 in the three sets of upper and lower grippers 80L, 82L located on a first side of FIG. 13. The computer system 26 may then begin the tensile test on the first three film specimens 54. While the tensile test is proceeding with the film specimens in the set of grippers 80L, 82L, the material holder system 14 may return to the cutting device 16, retrieve three more film specimens 54, and then place them in the three sets of upper and lower grippers 80R, 82R on a second side of FIG. 13. The material holder system 14 may move the second set of film specimens 54 through the material image analyzer system 18 and/or material thickness measurement system 20 before delivering them to the set of grippers 80R, 82R on the second side of FIG. 13. The testing of the film specimens in grippers 80R, 82R may be started. During the testing procedure, the material holder system 14 may remove tested film specimens from the grippers 80L, 82L on the first side of FIG. 13 and dispose of them, return to the tensile testing apparatus 22, and repeat the disposal process with the film specimens located in the grippers 80R, 82R on the right hand side of FIG. 12.

According to an alternative embodiment, the material holder system 14 may deliver all six film specimens to the tensile testing apparatus 22 at the same time. That is, the material holder system 14 may place the first three film specimens in the set of upper and lower grippers 80L, 82L on the first side of FIG. 13. Still holding the remaining three film specimens, the material holder system 14 may move to the second set of upper and lower grippers 80R, 82R, and place the film specimens in the respective sets of grippers. After the material holder system 14 has sufficiently retracted from the grippers 80R, 82R, the testing may be started on all six film specimens.

Figure 16:
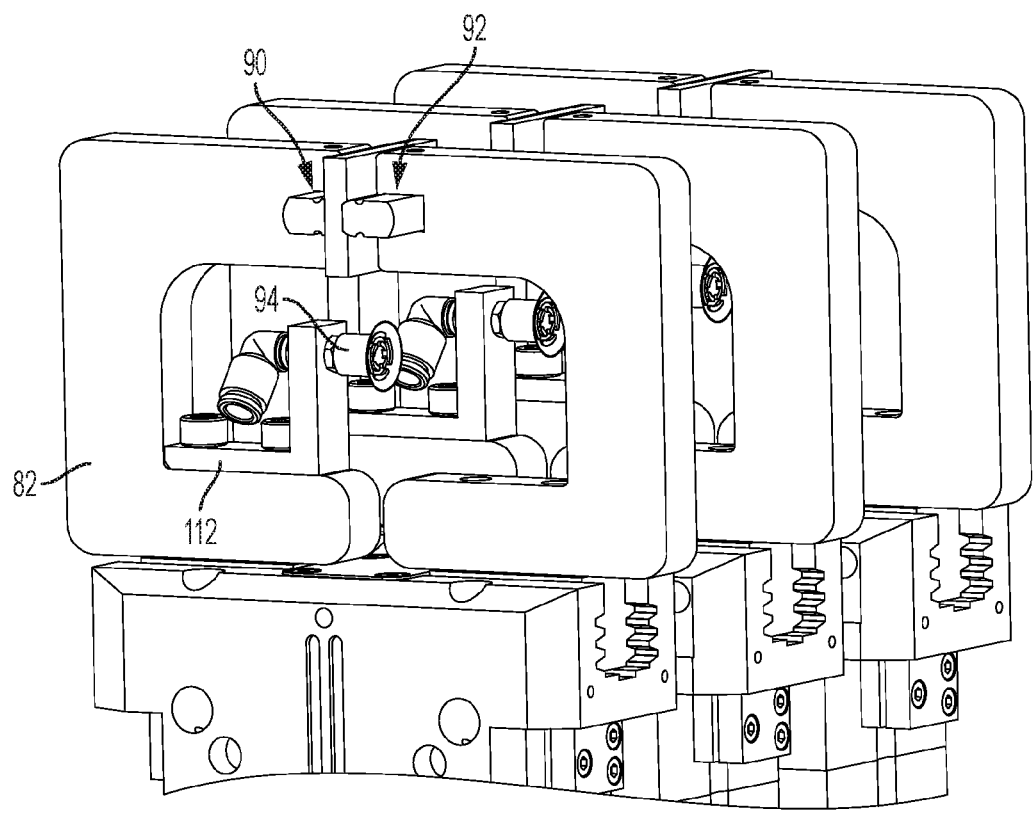
FIG. 16 shows a three-dimensional perspective view of components of a tensile testing apparatus, according to an embodiment of the present disclosure.

FIG. 16 shows a three-dimensional perspective view of the lower grippers 82, according to an embodiment of the present disclosure. Each lower gripper 82 may include a vacuum cup 94. The vacuum cup 94 may be attached to the lower gripper 82 with a bracket 112. The vacuum cup 94 may be located such that it aligns with a film specimen 54 when the film specimen 54 is located in the lower gripper 82. For example, the vacuum cup 94 may be located along a bottom surface of lower gripper 82, below the line grips 90, 92. The vacuum may be supplied by a source attached to a rear of the vacuum cup 94. The vacuum cup 94 may be actuated after the tensile test has completed and prior to the lower grippers 82 opening. Thus, the vacuum cup 94 allows for the film specimen 54 to be held in place after the test has completed and the film specimen 54 has been broken or deformed. The robotic system 12 and material holder system 14 can collect the film specimens from the lower grippers 82 since they are held in place by vacuum cup 94. Although the vacuum cups 94 are depicted on the lower grippers 82, they may also be placed on the upper grippers 80 to hold the top portion of the specimens after breaking or deforming.

FIG. 17 shows a three-dimensional perspective view of a portion of upper grippers 80, according to an embodiment of the present disclosure. FIG. 17 depicts the load cell 84 attached to mounting blocks 106. A layer of dampening material 96 is located between mounting blocks 106 and load mounts 98. A bracket 104 may be attached by columns 108 to the dampening material 96. The bracket 104 may attach the entire assembly (load cells 84, upper grippers 80, mounting blocks 106, and dampening material 96) to the upper frame 86. The bracket 104 may be attached to the upper frame 86 in a known manner, such as with a fastener. The dampening material 96 may absorb any vibrations due to film specimen breakage. An exemplary type of dampening material 96 may be ISODAMP C-1002™. The dampening material may be a 1" thick layer. Alternatively, the dampening material may be selected in a material type and thickness which prevents vibrations from transferring between the specimens during testing. This arrangement reduces vibrational feedback during testing.

Figure 18:
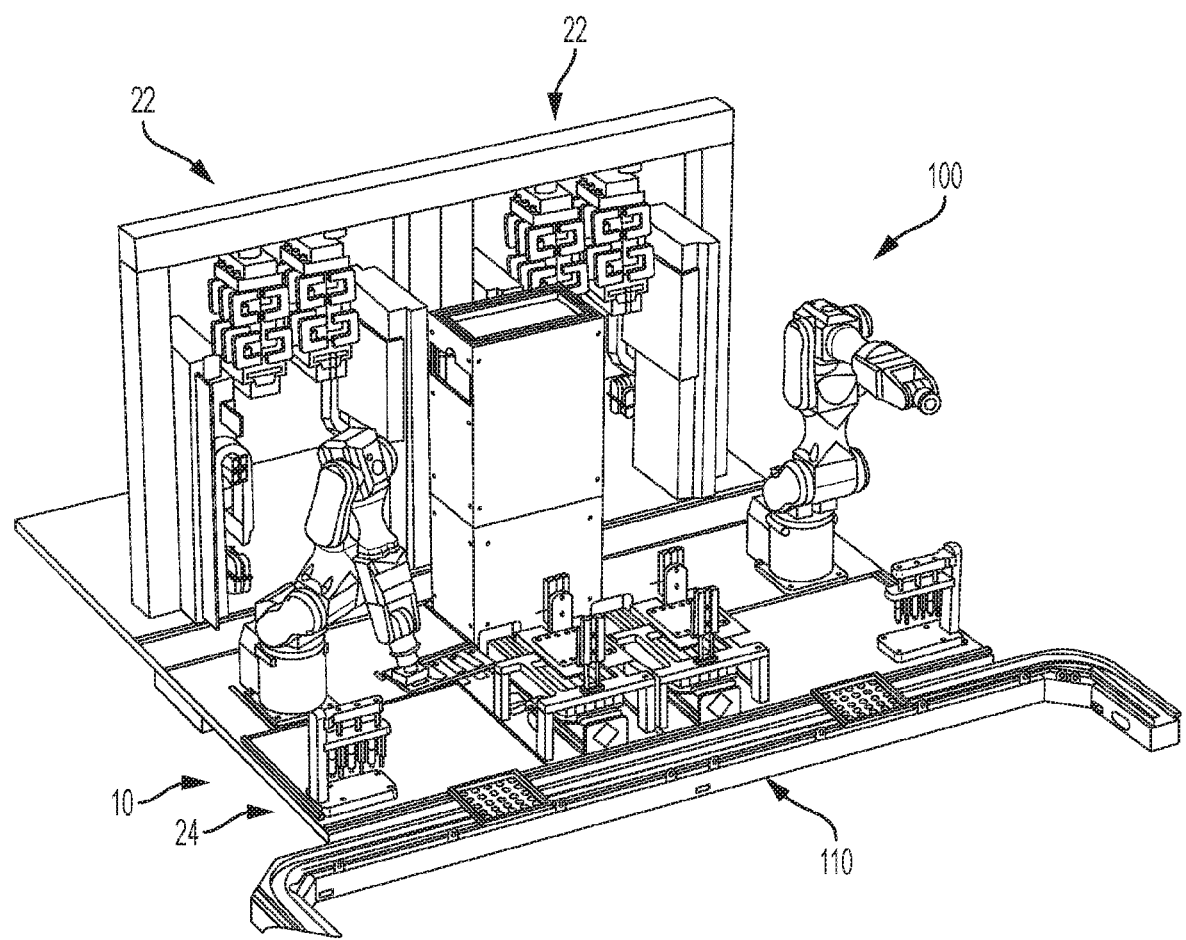
FIG. 18 shows a three-dimensional perspective view of a tensile testing system, according to an embodiment of the present disclosure.

FIG. 18 shows a three-dimensional perspective view of a first tensile testing system 10 and a second tensile testing system 100 which may be located near one another (e.g., on a common work surface 24 or other framework). This configuration can allow two tensile testing apparatuses 22 to perform tensile testing substantially at the same time, thus increasing the throughput of the overall system. A delivery system 110 may also be provided. The delivery system 110 may include trays which deliver samples to the work surface 24 for testing with the tensile testing systems 10, 100. The delivery system 110 may deliver a film sample 52 to a location in front of the tensile testing system 10 or 100 where the robotic system 12 and material holder system 14 may retrieve the film sample from the tray and proceed through the steps of the testing procedure.

According to embodiments of the present disclosure, the testing procedure for the tensile testing system 10 may include the following steps:
  (a) Operating the robotic system 12 to use the material holder system 14 to pick up a film sample,
  (b) cutting the film sample from a 6"×6" (152 mm×152 mm) square into six 1"×6" (25 mm×152 mm) film specimens using the cutting device 16,
  (c) measuring a thickness of the film specimens using the material thickness measurement system 20,
  (d) placing the film specimens into the tensile testing apparatus 22, and
  (e) stretching the film specimens, measuring the film characteristics of interest, and disposing of the tested film specimens.
  (f) Optionally, the testing procedure may include performing a material image analysis of the film specimens using the material image analyzer system 18.

With respect to step (a), a 6"×6" (152 mm×152 mm) film sample is transported to the work surface 24 via a transport system. The specimen can have a sample identifier to associate the data obtained during the various tests with the film sample. For example, the film sample can be associated with a Library ID and/or can be correlated to a file naming convention. The robotic system 12 moves the material holder system 14 near the film sample on the transport system. With the vacuum cups 38 facing in a downward direction, the 6"×6" (152 mm×152 mm) film sample is gripped with the vacuum cups 38, such that the material holder system 14 and vacuum cups 38 are located above the film sample.

With respect to step (b), the robotic system 12 moves material holder system 14 with the gripped 6"×6" (152 mm×152 mm) film sample to the cutting device 16. The robotic system 12 places the material holder system 14 (gripping the 6"×6" (152 mm×152 mm) film sample) between the pressure plate 50 and the film support plate 42. The material holder system 14 lowers the 6"×6" (152 mm×152 mm) film sample into the cavity 44 of the film support plate 42. The robotic system 12 removes the material holder system 14 from between film support plate 42 and pressure plate 50. The pressure plate 50 is lowered with pneumatic cylinder 46 such that the film sample is gripped between the pressure plate 50 and the film support plate 42 (e.g., with the assistance of mating tongues 66 and grooves 64). The linear actuator 40 is actuated to move blades 56 to cut the film sample. The film sample is thus cut, from a 6"×6" (152 mm×152 mm) film sample into, for example, 1"×6" (25 mm×152 mm) film specimens. Subsequently, the vacuum cups 68 are activated to hold the 1"×6" (25 mm×152 mm) film specimens in place as the pneumatic cylinder 46 raises the pressure plate 50 to open the cutting device 16.

The robotic system 12 now moves the material holder system 14 to retrieve the 1"×6" (25 mm×152 mm) film specimens. The material holder system 14 is located between the film support plate 42 and the pressure plate 50. The robotic system 12 then lowers the material holder system 14 such that the vacuum cups 38 of the material holder system 14 are located adjacent to the film specimens. The vacuum cups 38 are actuated, that is, the vacuum suction is turned on. The film specimens are then gripped with the vacuum cups 38 of the material holder system 14. At this time, the vacuum cups 68 of the film support plate 42 may be released. At this time, the film specimens are no longer held in the film support plate 42 and the robotic system 12 and material holder system 14 may manipulate the film specimens to the next step in the tensile testing system 10. Although the present disclosure discusses 6"×6" (152 mm×152 mm) film samples cut into six 1"×6" (25 mm×152 mm) film specimens, the material holder system may be capable of carrying any number of samples and specimens, having a variety of different sizes from the cutting device 16 to the subsequent stations in the tensile testing system 10. Although FIG. 3 depicts three of the 1"×6" (25 mm×152 mm) film specimens being held by the material holder system 14, it is to be understood that alternative embodiments may provide for all six 1"×6" (25 mm×152 mm) film specimens to be moved simultaneously. The robotic system 12 may move the material holder system 14 to move the film specimens from the cutting device 16 to the material image analyzer system 18.

With respect to step (c), the robotic system 12 moves the material holder system 14 holding the film specimens from the material image analyzer system 18 to the material thickness measurement system 20. The robotic system 12 and material holder system 14 locate the film specimens between the contact surfaces 70a, 70b. The shafts 76 linked to sensors 72 are extended to move the contact surface 70b upward. The film specimens may be held in place between the contact surfaces 70a, 70b. The sensor 72 may measure the difference between the extended contact surface 70b and the upper contact surface 70a to measure the thickness of the film specimens. Although three thickness measurement sensors 72 are depicted, it is understood that when material holder system 14 is constructed so as to handle six film specimens, then six sensors 72 may be provided such that all six film specimens may be measured for thickness simultaneously, or substantially simultaneously. Alternatively, the material holder system 14 may be moved such that the first, third, and fifth film specimens are measured for thickness first. Then the material holder system 14 may be moved to locate the second, fourth, and sixth film specimens between the contact surfaces 70a, 70b and their thicknesses may be measured.

With respect to step (d), the robotic system 12 moves the material holder system 14, holding the 1"×6" (25 mm×152 mm) film specimens to the tensile testing apparatus 22. The robotic system 12 locates the three film specimens between the line grips 90 and 92 of upper gripper 80 and lower gripper 82 (as seen in FIG. 14). A pneumatic operator then actuates the upper grippers 80 and lower grippers 82 to close the line grips 90 and 92. The line grips 90, 92 of the respective upper gripper 80 and lower gripper 82 now grip opposing ends of a 1"×6" (25 mm×152 mm) film specimen to be tested. The vacuum cups 38 of the material holder system 14 are released from the film specimens. The robotic system 12 retracts the material holder system 14 from between the upper grippers 80 and lower grippers 82. The robotic system 12 and material holder system 14 may then return to the three film specimens which were left in the cutting device 16 and repeat steps (c), (d), while step (e) is performed on the first three film specimens placed in the tensile testing apparatus 22. Thus, the three film specimens are placed in the tensile testing apparatus 22 in a simultaneous, or substantially simultaneous manner, with the tensile testing of another three film specimens.

According to an alternative sequence of operation, the material holder system 14 aligns a first 1"×6" (25 mm×152 mm) film specimen with a first set of upper and lower grippers 80, 82. The pneumatic operator actuates that set of grippers to close. The vacuum cups 38 on the material holder system 14 are released only from the gripped film specimen. The material holder system 14 may then be moved to align a second 1"×6" (25 mm×152 mm) film specimen with a second set of upper and lower grippers 80, 82. The pneumatic operator actuates the second set of grippers to close. The vacuum cups 38 on the material holder system are released only from the second gripped film specimen. The material holder system 14 may then be moved to align a third 1"×6" (25 mm×152 mm) film specimen with a third set of upper and lower grippers 80, 82. The pneumatic operator actuates the third set of grippers to close. The vacuum cups 38 are released only from the third gripped film specimen. Thus, according to this embodiment, the three film specimens are placed in the tensile testing apparatus 22 in a sequential manner.

In an embodiment where six 1"×"6 (25 mm×152 mm) film specimens are held by the material holder system 14, the first three film specimens may be placed in a first set of upper and lower grippers 80R, 82R or 80L, 82L (FIG. 13) in one of the previously described manners. Then, the robotic system 12 and material holder system 14 may move to the other of the set of upper and lower grippers 80L, 82L or 80R, 82R (FIG. 13), and the remaining three 1"×6" (25 mm×152 mm) film specimens may be placed therein in the same manner as the first three film specimens. The robotic system 12 subsequently retracts the material holder system 14 from the upper grippers 80 and lower grippers 82.

With respect to step (e), the lower frame 88 of the tensile testing apparatus 22 may be actuated to move downward at a controlled rate, thus stretching each 1"×6" (25 mm×152 mm) film specimen gripped in between an upper gripper 80 and a lower gripper 82. The lower frame 88 can be moved downward until all three film specimens have been broken or until the lower frame 88 has reached the lowest position and the film specimens have been deformed. During movement of the lower frame 88, each load cell 84 measures the force exerted thereon by the respective upper gripper 80. In some tests, some or all of the film specimens may be broken into a first portion gripped by upper gripper 80 and a second portion gripped by lower gripper 82. In some tests, some or all of the film specimens may not be broken, but instead may be stretched such that they are deformed and reach maximum elongation. Load and displacement data for each film specimen is recorded by computer system 26 for analysis.

After the testing has been completed, vacuum cups 94 located in upper gripper 80 and lower gripper 82 may be actuated to hold the first portion and second portion of the film specimen. The robotic system 12 may move the material holder system 14 between the upper grippers 80 and lower grippers 82 to align with the tested film specimens. The vacuum cups 38 on the material holder system 14 may be actuated to hold the film specimens and the vacuum cups 94 on the grippers may be released. The material holder system 14 now holds the tested film specimens. The robotic system 12 may move the material holder system 14 to a disposal station where the vacuum cups 38 are released and the film specimen is allowed to fall into a disposal container.

The disposal site may include a disposal container and a disposal mechanism, such as a brush or puff of air, to dislodge the film from the material holder system 14. The material holder system 14 may be moved against the disposal mechanism to dislodge the tested specimen from the vacuum cups 38. Once dislodged, the tested specimen may fall into the disposal container.

After disposal of the tested film specimens, the robotic system 12 and material holder system 14 may return to step (a) and retrieve another 6"×6" (152 mm×152 mm) film sample from the transport system and begin steps (a) through (e) again. Such continuous operation of the robotic system 12 and tensile testing system 10 allows for high throughput film testing.

According to embodiments, and prior to any of steps (b), (c), and (d), the film specimens may be moved to the material image analyzer system 18. The film specimens are analyzed for defects and irregularities using the material image analyzer system 18. The width of the film specimens are measured by the material image analyzer system 18. The computer system 26 may collect and store image information obtained with the material image analyzer system 18. The data may be stored on a master database on the computer system 26 or in communication with the computer system 26. The step of analyzing with the material image analyzer system 18 may be omitted.

Although the process is described in the above order, it will be recognized that the order may be altered. According to embodiments, the order of the steps may be chosen, for example, based on proximity of the equipment to promote efficiency.

In an embodiment, the computer system 26 in communication with the tensile testing apparatus 22 is configured to collect or acquire force data and displacement data from the tensile testing apparatus 22. The computer system 26 includes a user interface to allow the user to enter test parameters such as the identification of the plastic film so that the results can be stored into a database linking it to the correct identification. The computer can also receive and store data from the material thickness measurement system 20 and material image analyzer system 18. The user interface also allows changes to test parameters such as distance, speed, and acceleration. The computer system 26 may control both the robotic system 12 and tensile testing apparatus 22. The data acquired with respect to the film specimens may be stored in master database on the computer system 26 or in communication with the computer system 26. The data may include thickness measurement, image analysis, force profiles, tensile test data, irregularities or defects, etc.

The load exerted and the displacement of the grippers is measured and recorded during the tensile test. The film specimen's tensile strength at yield and break are measured and recorded during the tensile test. These variables may be used to calculate a suite of result metrics, including yield stress, yield strain, break stress, break strain, peak load, energy to break, and energy per unit volume. Since force per extension and displacement are so closely related in tensile testing, a controller used to store these values simultaneously may be used. An example of such a controller is an Aerotech controller. The controller may store load cell force values and encoder readings simultaneously, without the latency of a secondary system. Once the test has completed, the computer system 26 may move the data off the controller and analyze it. Once the data has been processed, it may be stored on the computer system 26. The computer system 26 may also determine overall statistics for a batch of material samples. That is, the values for all of the individual samples of a batch may be averaged and outliers flagged and/or removed from the batch analysis.

The term "computer system" is used herein to encompass any data processing system or processing unit or units. The computer system may include one or more processors or processing units. The computer system can also be a distributed computing system. The computer system may include, for example, a desktop computer, a laptop computer, a handheld computing device such as a PDA, a tablet, a smartphone, etc. A computer program product or products may be run on the computer system to accomplish the functions or operations described in the above paragraphs. The computer program product includes a computer readable medium or storage medium or media having instructions stored thereon used to program the computer system to perform the functions or operations described above. Examples of suitable storage medium or media include any type of disk including floppy disks, optical disks, DVDs, CD ROMs, magnetic optical disks, RAMs, EPROMs, EEPROMs, magnetic or optical cards, hard disk, flash card (e.g., a USB flash card), PCMCIA memory card, smart card, or other media. Alternatively, a portion or the whole computer program product can be downloaded from a remote computer or server via a network such as the internet, an ATM network, a wide area network (WAN) or a local area network.

Stored on one or more of the computer readable media, the program may include software for controlling a general purpose or specialized computer system or processor. The software also enables the computer system or processor to interact with a user via output devices such as a graphical user interface, head mounted display (HMD), etc. The software may also include, but is not limited to, device drivers, operating systems and user applications. Alternatively, instead or in addition to implementing the methods described above as computer program product(s) (e.g., as software products) embodied in a computer, the method described above can be implemented as hardware in which for example an application specific integrated circuit (ASIC) or graphics processing unit or units (GPU) can be designed to implement the method or methods, functions or operations of the present disclosure.

The invention claimed is:

1. A system for analyzing a physical characteristic of a film specimen, the system comprising:
   a cutting device, wherein the cutting device comprises a linear actuator and at least one blade configured to cut a film sample into one or more film specimens;
   a material holder system configured to hold the film specimen;
   a tensile testing system configured to stretch the film specimen and determine a physical characteristic of the film specimen; and
   a movable system coupled to the material holder system and configured to move the held film specimen to be analyzed or tested between stations,
   wherein the movable system is configured to move the held film specimen in the material holder system to the tensile testing system.

2. The system of claim 1, further comprising a computer system configured to control the movable system, the material holder system, and the tensile testing system.

3. The system of claim 1, wherein the movable system comprises an articulating-arm robotic arm system.

4. The system of claim 1, wherein the material holder system includes a vacuum suction system configured to hold the film specimen through vacuum suction.

5. The system of claim 1, wherein the tensile testing system comprises at least a first gripper and a second gripper, wherein the first gripper and second gripper are configured to hold the film specimen therebetween.

6. The system of claim 5, wherein the first gripper is movable with respect to the second gripper to stretch the film specimen.

7. The system of claim 6, wherein the tensile testing system further comprises a load cell configured to measure forces applied to the first gripper or the second gripper during stretching of the film specimen.

8. The system of claim 1, wherein the cutting device further comprises a film support plate and a pressure plate, wherein at least one tongue is located in one of the film support plate and the pressure plate, and at least one groove is located in the other of the film support plate and the pressure plate, wherein the at least one tongue engages the at least one groove during cutting to hold the film specimen therebetween and in place.

9. The system of claim 8, wherein the film support plate comprises at least one vacuum cup configured to hold the one or more film specimens after being cut.

10. The system of claim 1, wherein the tensile testing system further comprises at least one vacuum cup configured for holding the film specimen after the film specimen has been stretched.

11. The system of claim 1, further comprising a material thickness measurement system configured to measure a thickness of the film specimen.

12. The system of claim 1, further comprising a material image analyzer system configured to detect a defect in the film specimen.

13. The system of claim 12, wherein the image analyzer system is configured to measure a width of the film specimen.

14. A method for analyzing a physical characteristic of a film sample, the method comprising:
   holding the film sample with a material holder system connected to a movable system;
   testing a physical characteristic of the film sample with a tensile testing system; and
   moving the material holder system holding the film sample to the tensile testing system with the movable system;
   wherein testing a physical characteristic of the film sample with the tensile testing system is performed simultaneously with at least one of:
   cutting a second film sample into a plurality of film specimens;
   detecting defects in a second film sample with an image analyzer system;
   measuring width of the second film sample with the image analyzer system; or
   measuring thickness of a second film sample with a thickness measurement system.

15. The method of claim 14, wherein testing a physical characteristic of the film sample comprises:
   gripping a first portion of the film sample in a first gripper of the tensile testing system;
   gripping a second portion of the film sample in a second gripper of the tensile testing system;
   moving the first gripper and the second gripper with respect to one another to stretch the film sample; and
   measuring a force exerted on one of the first gripper and the second gripper during stretching.

16. The method of claim 14, wherein the film sample is a cut piece from an original film source.

* * * * *